US012582355B2

(12) United States Patent
Mostafaei et al.

(10) Patent No.: US 12,582,355 B2
(45) Date of Patent: Mar. 24, 2026

(54) HEARING DEVICE WITH OPTICAL SENSOR FOR DETERMINING A TISSUE PROPERTY

(71) Applicant: SONOVA AG, Staefa (CH)

(72) Inventors: Maryam Mostafaei, Wallisellen (CH); Konstantin Silberzahn, Meilen (CH)

(73) Assignee: Sonova AG, Staefa (CH)

(*) Notice: Subject to any disclaimer, the term of this patent is extended or adjusted under 35 U.S.C. 154(b) by 1051 days.

(21) Appl. No.: 17/690,875

(22) Filed: Mar. 9, 2022

(65) Prior Publication Data

US 2022/0287639 A1 Sep. 15, 2022

(30) Foreign Application Priority Data

Mar. 15, 2021 (EP) ..................................... 21162509

(51) Int. Cl.
  *A61B 5/00* (2006.01)
  *A61B 5/1455* (2006.01)
  *H04R 25/00* (2006.01)

(52) U.S. Cl.
  CPC .......... *A61B 5/6817* (2013.01); *A61B 5/1455* (2013.01); *A61B 5/7214* (2013.01);
  (Continued)

(58) Field of Classification Search
  CPC . A61B 5/6817; A61B 5/7214; A61B 2562/04; A61B 5/02427; A61B 5/14552;
  (Continued)

(56) References Cited

U.S. PATENT DOCUMENTS

2003/0233051 A1* 12/2003 Verjus .................... A61B 5/721
  600/528
2008/0146890 A1* 6/2008 LeBoeuf .............. A61B 5/4839
  600/300
(Continued)

FOREIGN PATENT DOCUMENTS

EP    2077091 A2    7/2009
EP    2932729 A1    10/2015
(Continued)

OTHER PUBLICATIONS

"Extended European Search Report received in EP Application No. 21162509.0 on Aug. 17, 2021".

*Primary Examiner* — Abid A Mustansir
(74) *Attorney, Agent, or Firm* — ALG Intellectual Property, LLC

(57) ABSTRACT

A hearing device includes a housing configured to be worn at an ear of a user; an output transducer configured to provide an audio signal to the user; a light source configured to provide light emitted from a light emission area at the housing, the light illuminating an illumination volume extending into tissue at the ear when the housing is worn at the ear; and a first photodetector configured to detect a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area.

20 Claims, 11 Drawing Sheets

(52) U.S. Cl.
CPC ......... *H04R 25/604* (2013.01); *H04R 25/609*
(2019.05); *H04R 25/65* (2013.01); *A61B
2562/04* (2013.01); *H04R 2225/021* (2013.01);
*H04R 2225/025* (2013.01)

(58) Field of Classification Search
CPC . A61B 5/021; A61B 5/02416; A61B 5/02438;
A61B 5/14507; A61B 5/14532; A61B
5/6803; A61B 5/145; H04R 25/604;
H04R 25/609; H04R 25/65; H04R
2225/021; H04R 2225/025; H04R 25/60;
A61N 1/36038
See application file for complete search history.

(56) References Cited

U.S. PATENT DOCUMENTS

| | | | |
|---|---|---|---|
| 2015/0182135 A1* | 7/2015 | Ma | G06F 1/163 |
| | | | 600/323 |
| 2017/0071518 A1* | 3/2017 | Xavier Da Silveira | |
| | | | A61B 5/14552 |
| 2020/0085326 A1* | 3/2020 | Fransen | H04R 1/2838 |
| 2021/0298670 A1 | 9/2021 | Roeck et al. | |

FOREIGN PATENT DOCUMENTS

| | | |
|---|---|---|
| WO | 2020060911 A1 | 3/2020 |
| WO | 2020192956 A1 | 10/2020 |

* cited by examiner

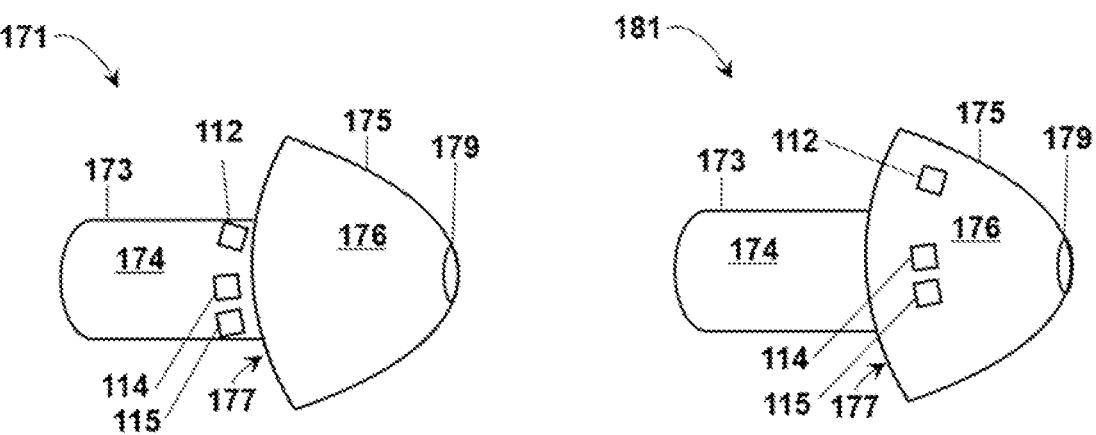
Fig. 4B                                        Fig. 4C
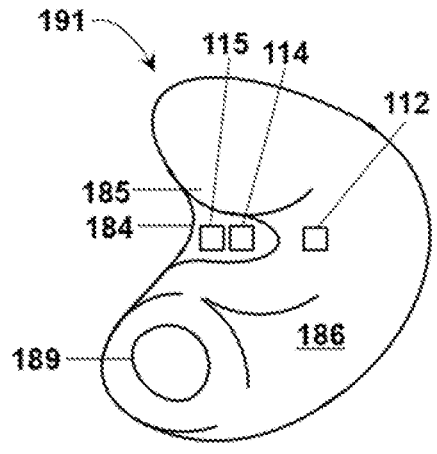
Fig. 4D
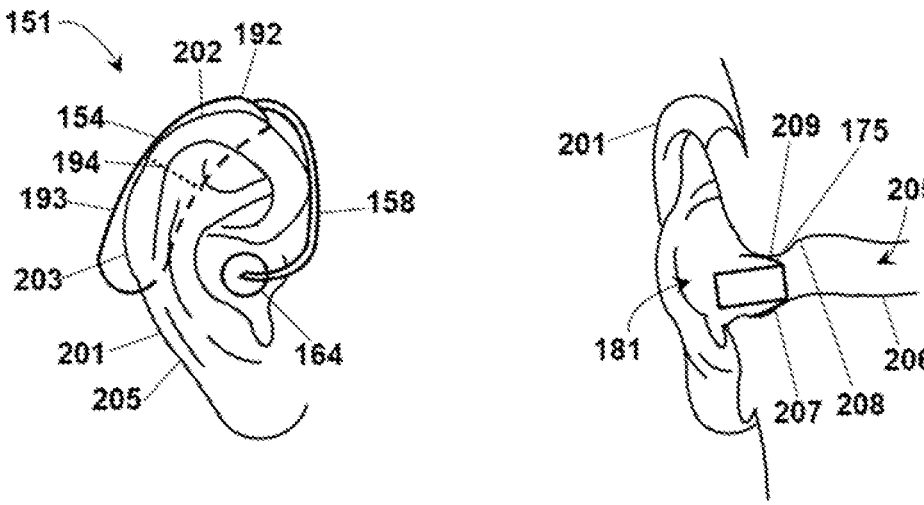
Fig. 5A                                        Fig. 5B

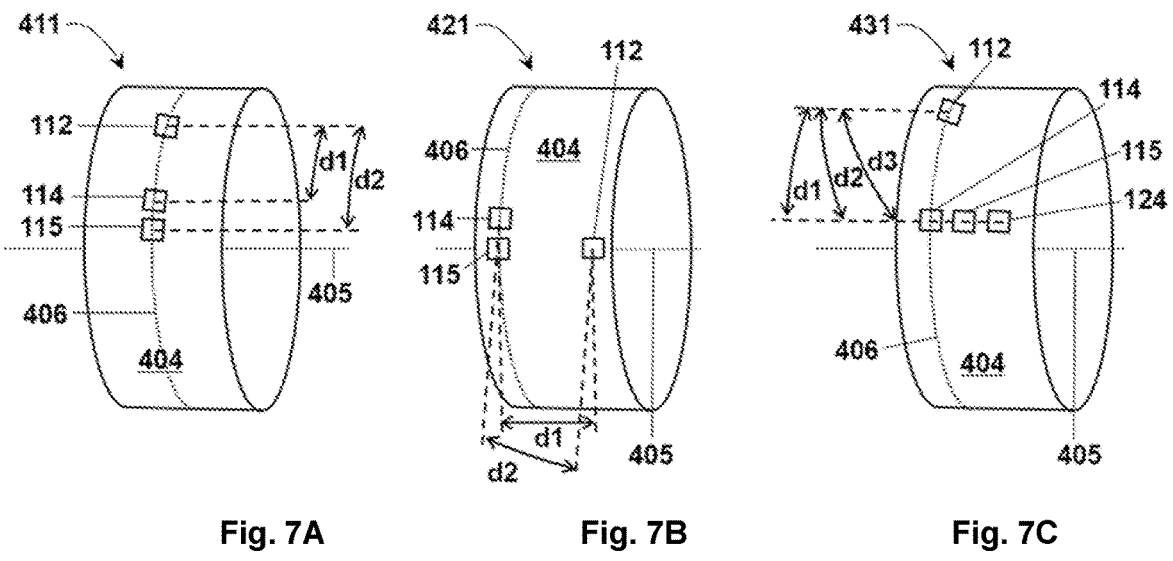
Fig. 7A                 Fig. 7B                 Fig. 7C
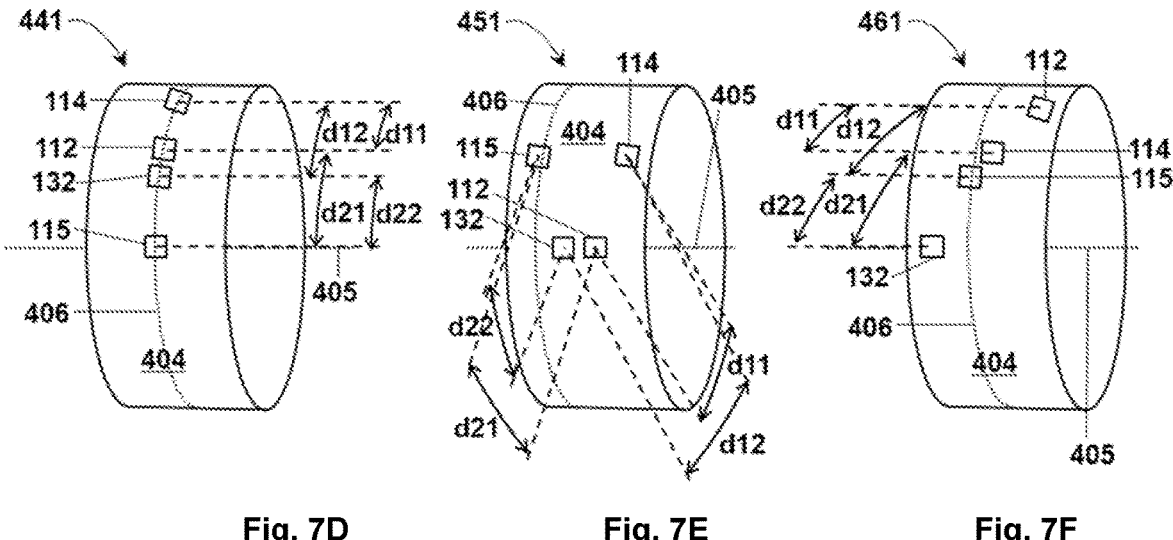
Fig. 7D                 Fig. 7E                 Fig. 7F

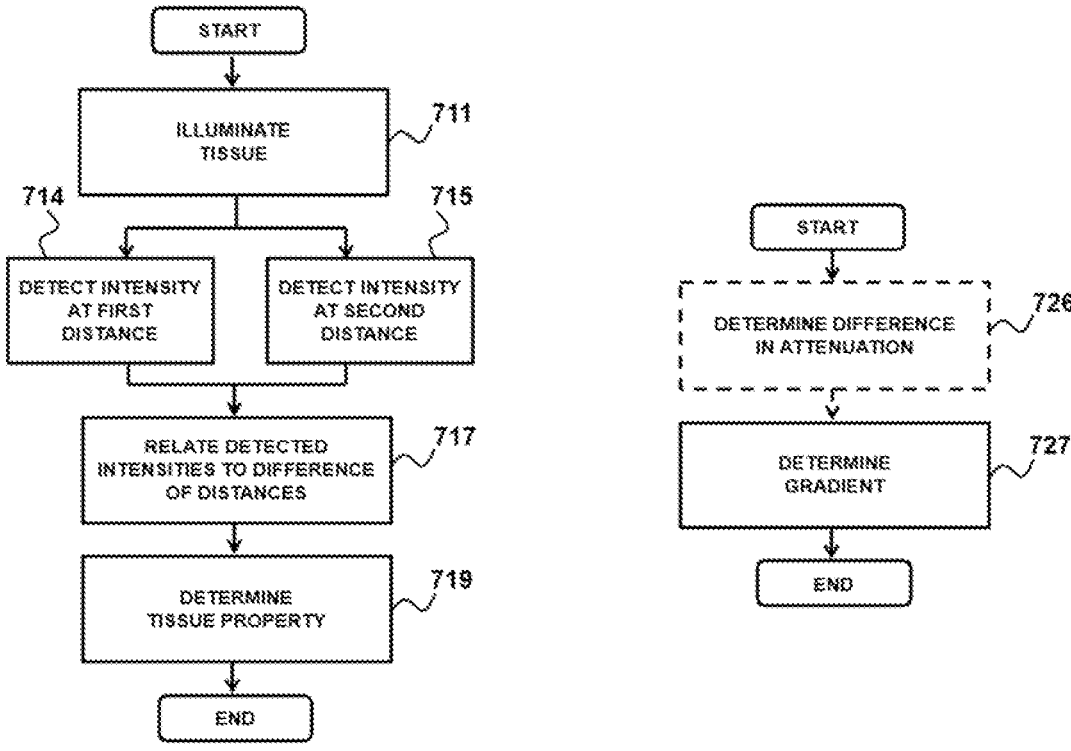
Fig. 10A
Fig. 10B
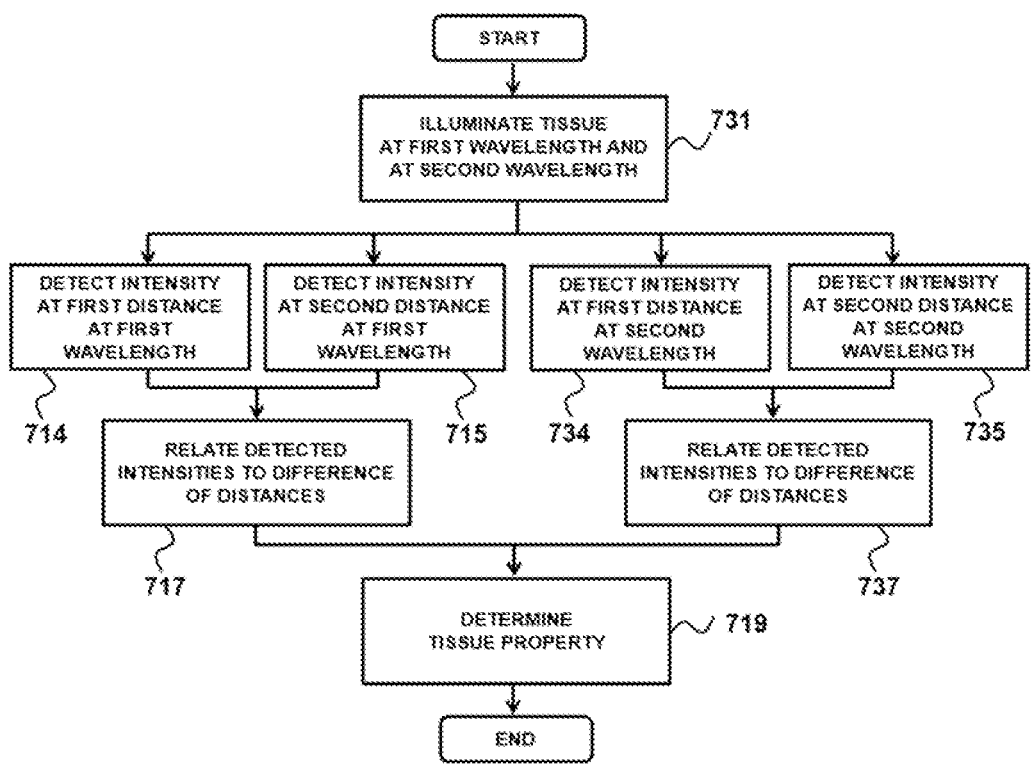
Fig. 10C

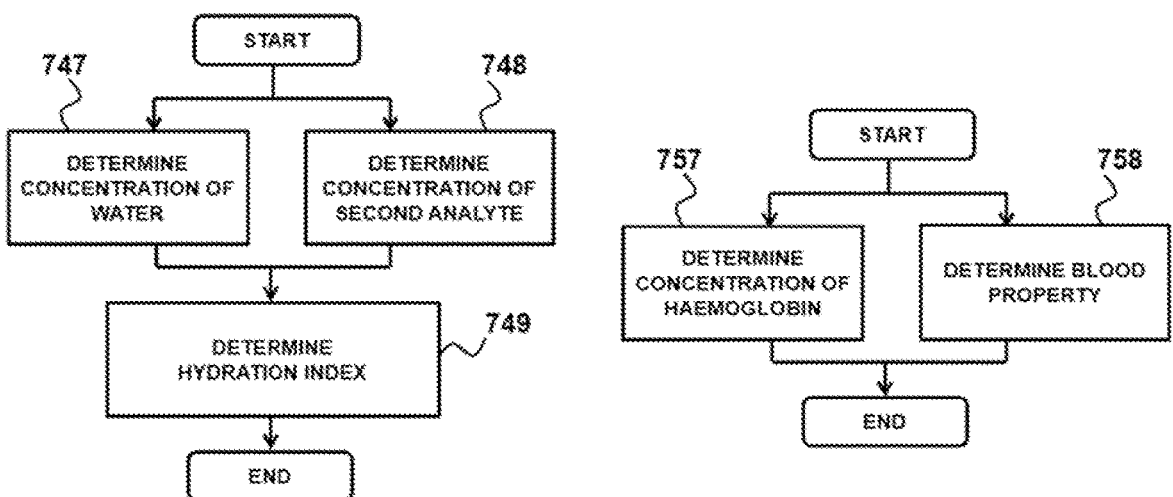
Fig. 10D                                    Fig. 10E
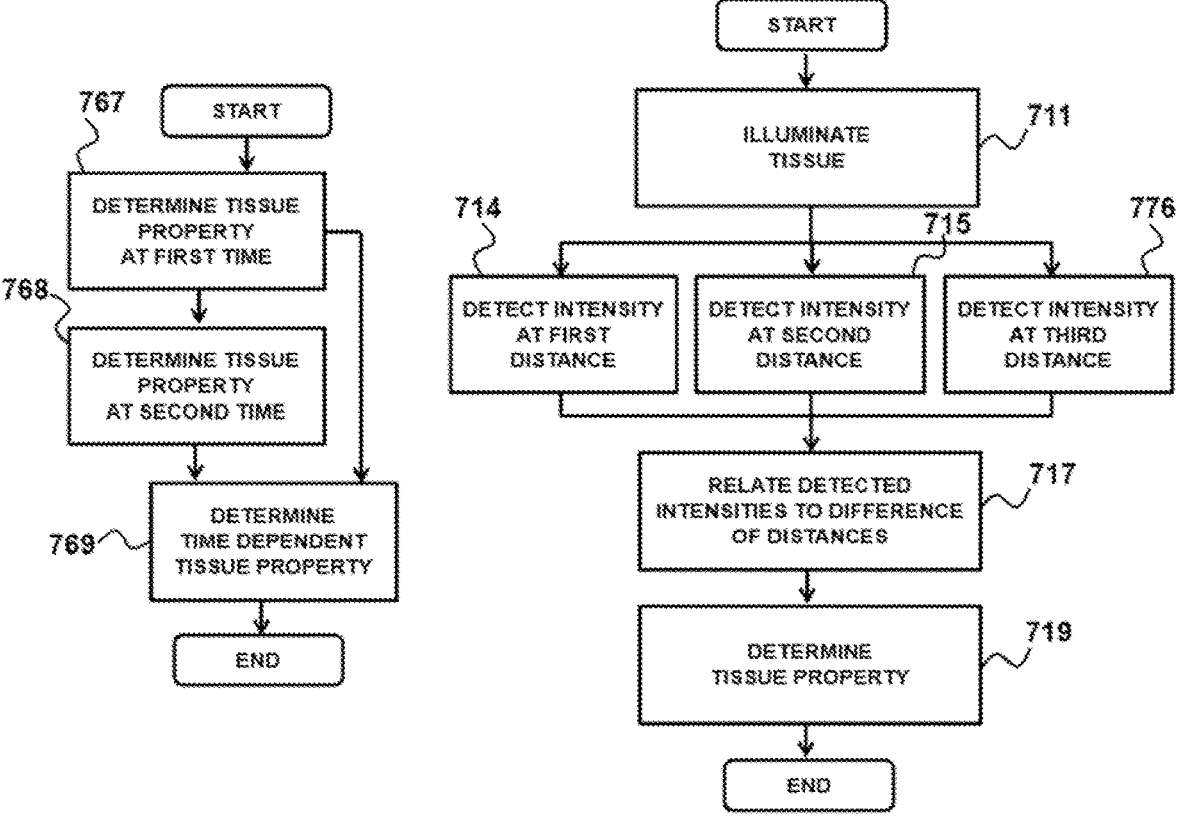
Fig. 10F                                    Fig. 10G

HEARING DEVICE WITH OPTICAL SENSOR FOR DETERMINING A TISSUE PROPERTY

RELATED APPLICATIONS

The present application claims priority to EP Patent Application No. EP21162509, filed Mar. 15, 2021, the contents of which are hereby incorporated by reference in their entirety.

BACKGROUND

Hearing devices may be used to improve the hearing capability or communication capability of a user, for instance by compensating a hearing loss of a hearing-impaired user, in which case the hearing device is commonly referred to as a hearing instrument such as a hearing aid, or hearing prosthesis. A hearing device may also be used to output sound based on an audio signal which may be communicated by a wire or wirelessly to the hearing device. A hearing device may also be used to reproduce a sound in a user's ear canal detected by a microphone. The reproduced sound may be amplified to account for a hearing loss, such as in a hearing instrument, or may be output without accounting for a hearing loss, for instance to provide for a faithful reproduction of detected ambient sound and/or to add sound features of an augmented reality in the reproduced ambient sound, such as in a hearable. A hearing device may also provide for a situational enhancement of an acoustic scene, e.g. beamforming and/or active noise cancelling (ANC), with or without amplification of the reproduced sound. Different types of hearing devices configured to be worn at an ear include earbuds, earphones, hearables, and hearing instruments such as receiver-in-the-canal (RIC) hearing aids, behind-the-ear (BTE) hearing aids, in-the-ear (ITE) hearing aids, invisible-in-the-canal (IIC) hearing aids, completely-in-the-canal (CIC) hearing aids, cochlear implant systems configured to provide electrical stimulation representative of audio content to a user, a bimodal hearing system configured to provide both amplification and electrical stimulation representative of audio content to a user, or any other suitable hearing prostheses. A hearing system comprising two hearing devices configured to be worn at different ears of the user is often referred to as a binaural hearing device.

Some hearing devices have been proposed which include an optical sensor for detecting physiological data. For example, such a device can include a light source and a photodetector to collect photoplethysmogram (PPG) data, as disclosed in international patent application No. PCT/EP2019/086071 and U.S. patent application No. U.S. Ser. No. 16/834,252. The light source is used to illuminate tissue inside the ear canal and the photodetector detects the light returning from the tissue at the device. Based on the detected light, it is possible to determine changes in light absorption caused by the blood flowing through the tissue during a heartbeat sequence. Physiological information such as heart rate, blood pressure, blood oxygen levels, breathing rate or volume, and the like can then be determined from this PPG data.

Incorporating the optical sensor into a hearing device, however, can produce movement artifacts in the PPG data caused by movements of the user wearing the hearing device leading to at least temporary displacements of the optical sensor relative to the monitored tissue inside the ear canal, and according changes of an amount and/or angle of the light coupled into the tissue and detected from the tissue. Those movement artifacts can degrade the quality of the PPG data and therefore reduce the reliability of the physiological information derived therefrom. An occurrence of movement artifacts could be even more pronounced when the optical sensor would be placed outside the ear canal, for instance behind the ear of the user in a hearing device comprising a behind-the-ear (BTE) part configured to be worn behind the ear, since in such an outer ear arrangement the optical sensor orientation can be even more susceptible to the user's movements. Yet the outer arrangement can be desirable for various reasons including a limited space inside the ear canal for accommodating the optical sensor in addition to other components, and also to obtain physiological information about tissue outside the ear canal which could be different from properties of the tissue illuminated inside the ear canal and/or hardly be derivable from the sensor data when illuminating the tissue inside the ear canal.

Further, it would be desirable to enhance the scope of physiological information that can de determined from the optical sensor data obtained at the ear level. For instance, people suffering from a hearing loss, which—to a large extent—include elderly people, are often affected by additional health problems including cardiovascular diseases, diabetes, and dehydration. The latter may be a rather underestimated risk factor which can lead to severe infections requiring hospitalization, and can also negatively impact the human ear function through altering mechanical properties of ear tissue, in particular a stiffening of soft tissue in the ear such as the round window membrane, and can also trigger other hearing malfunctions such as tinnitus, patulous eustachian tube disorder in the middle ear, fluid imbalance in the inner ear, and a endolymphatic hydrops disorder of the vestibular system. An early identification of dehydration issues may therefore be particularly desirable for people wearing a hearing instrument, and would be most conveniently performed by the hearing instrument itself. Even more convenient would be a monitoring of further health risks performed by the hearing device, for instance a glucose level relevant for diabetes and/or a blood pressure relevant for heart diseases, such that ideally only the hearing device would be required to perform the health monitoring of a hearing device user. Other users wearing a hearing device mainly for other purposes, such as entertainment or communication, are also increasingly interested in a monitoring of various health parameters in their daily life. The information needed for such a health monitoring, however, may be related to various layers of the tissue, which may include rather deep layers such as muscle tissue and/or brain tissue, and may include information different from a property of blood flowing through the tissue. For instance, desirable information may be related to a presence of an analyte or a plurality of analytes in the tissue, such as water, lipid, glucose, and/or haemoglobin contained in the tissue.

The data obtained by the optical sensor generally depends on characteristics of various sensor components and an assembly of the components in the sensor, which both can vary, at least within certain tolerances. In particular, manufacturing tolerances can arise when the components and/or the sensor are fabricated at a larger scale. For instance, a light emission intensity of an optical source and/or a detection sensitivity of a photodetector included in the optical sensor can be subject to those tolerances. Resulting variations in the sensor specifications can result in measurement uncertainties. The measurement uncertainties may be bypassed by calibrating the optical sensor after its assembly. Such a calibration, however, can be rather cumbersome and time consuming. It would therefore be desirable to provide the optical sensor in a way in which such an individually required calibration procedure could be omitted, and the measurements could still be performed by the optical sensor with high precision.

BRIEF DESCRIPTION OF THE DRAWINGS

Reference will now be made in detail to embodiments, examples of which are illustrated in the accompanying drawings. The drawings illustrate various embodiments and are a part of the specification. The illustrated embodiments are merely examples and do not limit the scope of the disclosure. Throughout the drawings, identical or similar reference numbers designate identical or similar elements. In the drawings:

FIGS. 4B-D schematically illustrate some embodiments of a housing of the hearing device illustrated in FIG. 1 configured to be at least partially inserted into an ear canal of a user;

FIGS. 5A, B schematically illustrate some positions at which the hearing device illustrated in FIG. 1 can be worn at an ear of a user;

FIGS. 7A-F schematically illustrate some configurations of a housing of the hearing device illustrated in FIG. 1 configured to be at least partially inserted into an ear canal of a user;

FIGS. 10A-H schematically illustrate some exemplary methods of operating a hearing device according to principles described herein.

DETAILED DESCRIPTION OF THE DRAWINGS

Figure 1:
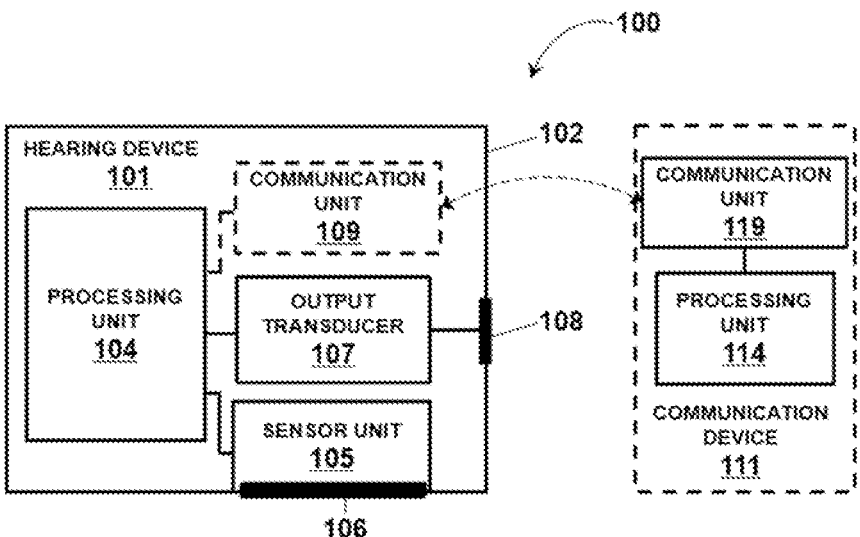
FIG. 1 schematically illustrates an exemplary hearing device comprising an output transducer and a sensor unit.

The disclosure relates to a hearing device comprising a housing configured to be worn at an ear of a user, an output transducer, a light source configured to provide light emitted from a light emission area at the housing to illuminate tissue at the ear, and a photodetector configured to detect a light intensity of light arriving from an acceptance volume extending into the tissue. The disclosure also relates to a hearing system comprising a hearing device and a communications device, and a method of determining a property of a tissue at an ear at which a housing of a hearing device is worn.

It is a feature of the present disclosure to avoid at least one of the above mentioned disadvantages and to equip a hearing device with an optical sensor accounting for an increased accuracy and/or reliability of the sensor data and/or allowing to obtain physiological information with increased and/or different content. It is a further feature to implement the optical sensor in a way to allow optimizing the hearing device performance, in particular to optimize valuable space occupied by the optical sensor in the hearing device, without compromising an accuracy and/or reliability of the optical sensor data. It is another feature to equip the optical sensor with the capability to provide the sensor data without the need of individually calibrating the sensor before its employment by the user. It is still another feature to equip the optical sensor with the capability to target specific layers of tissue at the ear, in particular a plurality of overlying tissue layers and/or including rather deep-lying tissue layers, and/or to collect information with regard to specific analytes contained in the tissue, in particular a plurality of different analytes. It is yet another feature to determine a hydration index of the targeted ear tissue based on the data collected by the optical sensor.

At least one of these features can be achieved by the hearing devices, hearing systems, methods, and/or computer-readable mediums described herein.

Accordingly, the present disclosure proposes a hearing device comprising a housing configured to be worn at an ear of a user; an output transducer configured to provide an audio signal to the user; a light source configured to provide light emitted from a light emission area at the housing, the light illuminating an illumination volume extending into tissue at the ear when the housing is worn at the ear; a first photodetector configured to detect a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area; a second photodetector configured to detect a second light intensity of light arriving from a second acceptance volume extending into tissue at the ear when the housing is worn at the ear such that a part of the emitted light scattered by the tissue into the second acceptance volume is contributing to the second light intensity, the second acceptance volume including a second reception area at the housing having a second distance from the light emission area different from the first distance, and a processing unit configured to determine a property of the tissue based on the first and second light intensity by taking into account the difference between the first and second distance.

In this way, by detecting the first light intensity of light received at the first distance and the second light intensity of light received at the second distance and taking into account the difference between the first and second distance when evaluating the first and second intensity, a reliability and/or accuracy of the determination of the property of the tissue can be improved. To illustrate, determining the property of the tissue can thus be based on multiple measurement data obtained from different tissue positions which can be related to each other by the previously known spatial relationship such that differences in the obtained data can be employed as an indicator for the property of the tissue, for instance as a sole indicator or in addition to other indicators derived from the measurement data. Since the multiple data is collected at the different distances having a fixed value, a property of the tissue derived from the differences in the data can be less prone to be influenced by movements of the user, which may be even more important in a more unstable positioning of the housing outside the ear canal, for instance behind the ear. To illustrate, movement artifacts may be equally present in each of the data collected at the different distances such that evaluating the differences in the collected data can be employed to reduce or disregard an impact of the user's movements in the data. Similarly, other disturbing effects equally present in the collected data, such as a cross talk of the light provided by the light source and detected by the photodetectors without passing through the tissue, e.g. by light reflected at a surface of the tissue, and background radiation of other light than the light emitted at the light emission area can be eliminated when evaluating the light intensities detected at the different distances.

Moreover, various tissue layers can be probed by such a sensor arrangement, which may depend on properties of the emitted light such as an intensity and/or wavelength but also on the selected first and second distance of the detectors to the light source, in order to get access to various kinds of information related to a property of the tissue. In particular, the sensor arrangement may be tailored to provide access to specifically desired information about the tissue and/or to provide the broadest possible information content, for instance by providing an appropriate distance of the detectors to the light source and/or providing for an appropriate wavelength of the light emitted by the light source, which may include different wavelengths absorbable by different analytes contained in the tissue and/or a continuous wavelength spectrum encompassing those different wavelengths.

Independently, the present disclosure proposes a hearing system and a communication device communicatively coupled to the hearing device, the hearing device including a housing configured to be worn at an ear of a user; an output transducer configured to provide an audio signal to the user; a light source configured to provide light emitted from a light emission area at the housing, the light illuminating an illumination volume extending into tissue at the ear when the housing is worn at the ear; a first photodetector configured to detect a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area; and a second photodetector, the second photodetector configured to detect a second light intensity of light arriving from a second acceptance volume extending into tissue at the ear when the housing is worn at the ear such that a part of the emitted light scattered by the tissue into the second acceptance volume is contributing to the second light intensity, the second acceptance volume including a second reception area at the housing having a second distance from the light emission area different from the first distance, wherein a processing unit is included in the communications device, the processing unit configured to determine a property of the tissue based on the first and second light intensity by taking into account the difference between the first and second distance.

Independently, the present disclosure proposes a method of determining a property of a tissue at an ear at which a housing of a hearing device is worn by a user, the method comprising emitting light provided by a light source from a light emission area at the housing, the light illuminating an illumination volume extending into tissue at the ear when the housing is worn at the ear; detecting, by a first photodetector, a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area; detecting, by a second photodetector, a second light intensity of light arriving from a second acceptance volume extending into tissue at the ear when the housing is worn at the ear such that a part of the emitted light scattered by the tissue into the second acceptance volume is contributing to the second light intensity, the second acceptance volume including a second reception area at the housing having a second distance from the light emission area different from the first distance; and determining, based on the first and second light intensity, the property of the tissue by taking into account the difference between the first and second distance.

Independently, the present disclosure proposes a non-transitory computer-readable medium storing instructions that, when executed by a processing unit included in the hearing device and/or communication device, cause the processing unit to perform said method.

Subsequently, additional features of some implementations of the hearing device and/or the hearing system and/or the method of determining a property of the tissue and/or the computer-readable medium are described. Each of those features can be provided solely or in combination with at least another feature. The features can be correspondingly provided in some implementations of the hearing device and/or the hearing system and/or the method and/or the computer-readable medium.

In some implementations, the processing unit is configured to determine, based on the first and second light intensity, a difference in an attenuation of the light emitted from the light emission area between the first reception area and the second reception area. It may also be that the sensor unit is configured to determine another quantity based on the first and second light intensity, for instance a difference of a reflectance at the first reception area and the second reception area and/or a reflectance and/or an attenuation of the emitted light at each the first reception area and the second reception area. The processing unit can be configured to relate the first and second light intensity and/or at least one of the quantities determined based on the first and second light intensity to the difference between the first and second distance to determine the property of the tissue. In some implementations, the processing unit is configured to determine, based on the first and second light intensity, a quantity other than the difference in attenuation, wherein the determining the property of the tissue may be fully or partially based on the other quantity.

In some implementations, the hearing device comprises a third photodetector configured to detect a third light intensity of light arriving from a third acceptance volume extending into tissue at the ear when the housing is worn at the ear such that a part of the light scattered by the tissue into the third acceptance volume is contributing to the third light intensity, the third acceptance volume including a third reception area at the housing having a third distance from the light emission area different from the first distance and the second distance, wherein the processing unit is configured to determine the property of the tissue based on the third light intensity in addition to the first and second light intensity. Such an arrangement may be employed to further enhance the information about the tissue by monitoring adjacent tissue compartments corresponding to the difference of the first and second distance, and the difference of the second and third distance. The property of the tissue may thus be determined by further taking into account the difference between the second distance and the third distance and/or the difference between the first distance and the third distance. In particular, a different penetration depth of the emitted light received at the different distances may be employed to gain additional information about the tissue. For example, different tissue compartments can be characterized by different concentrations of an analyte such as water, which may vary over time, and information about the relative concentrations may then be employed to determine the property of the tissue, e.g. a hydration status of the tissue. In addition, an accuracy and/or reliability of the measurement may be enhanced by providing the additional information at the third distance.

In some implementations, the light source is a first light source, the light emission area is a first light emission area, and the illumination volume is a first illumination volume, the hearing device further comprising a second light source configured to provide light emitted from a second light emission area at the housing at a distance from the first light emission area, the light provided by the second light source illuminating a second illumination volume extending into tissue at the ear when the housing is worn at the ear such that a part of the light emitted from the second light emission area scattered by the tissue into the first acceptance volume is contributing to the first light intensity detected by the first photodetector, and part of the light emitted from the second light emission area scattered by the tissue into the second acceptance volume is contributing to the second light intensity detected by the second photodetector, the first reception area having a distance from the second light emission area equal to said second distance, and the second reception area having a distance from the second light emission area equal to said first distance, wherein the first and second photodetector are configured to detect the first and second light intensity at a first time during which light is emitted from one of the first and second light emission area, and at a second time different from the first time during which light is emitted from the other of the first and second light emission area, and the processing unit is configured to determine the property of the tissue based on the first and second light intensity detected at the first time and at the second time.

In this way, a sensor unit having a symmetrical arrangement of the first and second reception areas relative to first and second light emission areas can be provided. The symmetrical arrangement can allow to obtain the measurement data in a twofold way including the first time, during which the light emitted from the first and second light emission area may be only emitted from the first light emission area, and the second time, during which the light emitted from the first and second light emission area may be only emitted from the second light emission area. In particular, the first and second light source may be configured such that the light provided by the first and second light source is only provided by one of the first and second light source during the first time, and only provided by the other of the first and second light source during the second time. The twofold information can be exploited to eliminate unknown parameters from the measurement results. For instance, the processing unit may be configured, based on the first intensity and the second intensity detected at the first time and at the second time, to calibrate the first intensity and second intensity with respect to the unknown parameters in a self-reliant way according to the twofold information obtained at the first and second time, in particular without the need of a preceding additional calibration relative to the unknown parameters before the measurement could be performed.

In some implementations, the light source is configured to provide the light at a constant intensity during a time interval in which the first light intensity is detected by the first photodetector and the second light intensity is detected by the second photodetector. In this way, a temporal behavior of the intensity of the emitted light can be kept constant during the time interval allowing to evaluate the first and second light intensity by disregarding a time dependency of the emitted light. This may be exploited to simplify determining a relationship between the light detected at the different distances by excluding temporal dependencies and only focusing on the spatial dependency governed by the difference between the first and second distance.

In some instances, the light source is configured to provide the light at the constant intensity during a first time interval in which the first and second light intensities are detected for a first time, and during a second time interval, in which the first and second light intensities are detected for a second time. In particular, the light source may be configured to provide the light in a temporal sequence of pulses at a constant intensity during each pulse. In this way, also a temporal resolution of the measurement data may be obtained, in addition to the spatial resolution which may be based on the first and second intensity detected for each time interval in which the light has been emitted at the constant intensity. In some instances, the constant light emission intensity may be varied in the subsequent time intervals. For instance, the constant intensity of subsequent emitted light pulses may be continuously altered, e.g. corresponding to a sine-wave. In this way, a tissue property may also be determined in a time-dependent manner.

In some instances, the first and second reception area are provided at least partially separate from one another at the housing. In particular, the first and second reception area may partially overlap at the housing. A center of the first reception area may then be separate from the second reception area, and a center of the second reception area may then be separate from the first reception area. In some instances, the first and second reception area separate from one another at the housing. An overlapping of the first and second reception area may thus be avoided, in particular to improve the of the quality of the data measured at the different distances with respect to the spatial information contained therein. Correspondingly, the third reception area may be provided at least partially separate from the first and second reception area at the housing, or separate from the first and second reception area at the housing. In some instances, the first and second light emission area are provided at least partially separate from one another at the housing. In particular, the first and second light emission area may partially overlap at the housing. The overlap may also be rather large, as long as the first and second light emission area each comprise a portion distant from the other, and the light is emitted at different times from the first and second light emission area. In some instances, the first and second reception area are separate from one another at the housing. An overlapping of the first and second light emission area may thus also be avoided, in particular to emit the light into distinct portions of the tissue which may increase the significance of the information obtained based on the light received at the second time, at which the light is emitted from the second light emission area, with respect to the light received at the first time, at which the light is emitted from the first light emission area, in order to employ the twofold measurement data for a self-calibration purpose.

In some implementations, the processing unit is configured to determine a concentration of an analyte contained in the tissue. In some instances, the analyte comprises water and/or lipid and/or haemoglobin and/or glucose. In some instances, the processing unit is configured to determine a concentration of at least two analytes contained in the tissue. In some instances, the processing unit is configured to determine a concentration of at least three analytes contained in the tissue. The property of the tissue determined by the processing unit may comprise the concentration of the at least one analyte. In some instances, the processing unit may be configured, based on the concentration of the first analyte and the concentration of the second analyte, a hydration index of the tissue. The property of the tissue determined by the processing unit may then comprise the hydration index of the tissue.

In some implementations, the property determined by the processing unit is a first property, the processing unit configured to determine a second property of the tissue based on the first intensity and/or second intensity, wherein the second property comprises a property of blood flowing through the tissue. For instance the property of blood may comprise an oxygen saturation index (SpO2) and/or a blood pressure and/or a heart rate and/or a blood sugar level.

In some implementations, the light source is configured to emit light at a first wavelength and at a second wavelength different from the first wavelength. In particular, the first wavelength and/or the second wavelength may be between 800 nm and 1650 nm. In some instances, the other of the two different wavelengths may be provided as a different wavelength comprised in these wavelengths. In some instances, the other of the two different wavelengths may be provided as a wavelength smaller than 800 nm, in particular a wavelength deviating from 660 nm by less than 20 nm. In particular, such a smaller wavelength may be employed to determine a property of blood flowing through the tissue.

In some instances, the light source comprises a first light source element configured to provide the light at the first wavelength, and a second light source element configured to provide the light at the second wavelength. In some instances, the light emission area comprises a first light emission area section configured to emit the light at the first wavelength, and a second light emission area section configured to emit the light at the second wavelength. In some instances, the first light emission area section and the second light emission area section are spaced from one another at the housing.

In some instances, the photodetector comprises a first photodetector element configured to detect the light intensity at the first wavelength, and a second photodetector element configured to detect the light at the second wavelength. In some instances, the reception area comprises a first reception area section configured to receive the light detectable by the photodetector at the first wavelength, and a second reception area section configured to receive the light detectable by the photodetector at the second wavelength. In some instances, the first reception area section and the second reception area section are spaced from one another at the housing.

In some implementations, the processing unit is configured to determine, based on the first intensity and the second intensity detected at the first wavelength, a concentration of a first analyte contained in the tissue, and, based on the first intensity and the second intensity detected at the second wavelength, a concentration of a second analyte contained in the tissue. The processing unit may then also be configured to determine, based on the concentration of the first analyte and the concentration of the second analyte, a hydration index of the tissue. In some implementations, the processing unit is configured to determine, based on the first intensity and the second intensity detected at the first and second wavelength, a concentration of an analyte contained in the tissue.

To illustrate, the first wavelength may correspond to a wavelength absorbable by water, which may be selected in a shorter wavelength range between 940 nm and 1000 nm, in particular 970 nm around which an absorption peak of water is centered, and/or in a longer wavelength range between 1300 nm and 1550 nm, in particular 1450 nm around which another absorption peak of water is centered. The shorter wavelength range between 940 nm and 1000 nm may offer the advantage of a larger penetration depth into the tissue and/or may be implemented at a lower cost. The longer wavelength range between 1300 nm and 1450 nm may offer the advantage of a higher absorption rate by the water, such that a sensitivity of the detection can be increased, and/or a lower contribution of other absorbing analytes contained in the tissue, such as melanin, haemoglobin, collagen, etc., which may mostly affect light emitted at the shorter wavelength range.

In some instances, the second wavelength also corresponds to a wavelength absorbable by water, which may be selected according to the wavelength range of the first wavelength, or in a different wavelength range. For instance, when the first wavelength is selected within the shorter wavelength range at the water absorption peak at 970 nm or within the longer wavelength range at the water absorption peak at 1450 nm, the second wavelength may be also selected within the same wavelength range to improve a resolution of the detection within this range, or within the other wavelength range to provide further evidence of the absorption by water. In this way, the accuracy of the detection of the analyte may be increased. For instance, a wavelength of an absorption peak of the analyte may be resolved by selecting the first wavelength and the second wavelength close to a value at which the absorption peak of the analyte is expected. In particular, an area under the expected absorption peak may be determined by integrating the light intensities detected at different wavelengths over the wavelength. A resolution of the absorption peak may be further enhanced based on at least a third light intensity emitted and detected at a third wavelength.

In some instances, the second wavelength corresponds to a wavelength absorbable by an analyte different from water. For instance, the second wavelength may be provided in a wavelength range deviating from 660 nm or 810 nm or 950 nm by at most 20 nm to account for an absorption of haemoglobin. The second wavelength may also be provided in a wavelength range deviating from 1200 nm by at most 30 nm to account for an absorption of lipid. The second wavelength may also be provided in a wavelength range deviating from 1450 nm by at most 50 nm to account for an absorption of glucose. In this way, an interaction of water with the analyte different from water may be analyzed. In particular, the second wavelength may deviate from a peak absorption wavelength of the analyte only to an extent allowing to determine an absorption of the light by the analyte that can also be attributed to the absorption mechanism of the analyte occurring at the peak absorption wavelength. In some instances, a property of blood flowing through the tissue may also be determined. The second wavelength may then be selected to correspond to a wavelength absorbable by the blood.

In some instances, the processing unit is configured to determine, based on the first and second intensity detected at a third wavelength in addition to the first and second intensity detected at the first and second wavelength, a concentration of a third analyte contained in the tissue, or a concentration of an analyte contained in the tissue may be determined by the processing unit based on the first and second intensity detected at the first wavelength and/or the first and second intensity detected at the second wavelength and the first and second intensity detected at the third wavelength. In this way, at least two of the above illustrated instances of exemplary embodiments may be combined.

In some instances, the first distance and the second distance extend in different directions at the housing. In this way, the difference between the first distance and the second distance may be provided rather small, and, at the same time a distance between the first and second reception area may also be kept rather small. In this way, a comparability of the first and second intensity may be improved which may account for determining the property of the tissue with a better accuracy and/or reliability. Moreover, the smaller distance of the first distance and the second distance may be kept at a value required to reach a desired penetration depth of the emitted light into the tissue. In some instances, the difference between the first distance and the second distance is at most 5 mm. In some instances, the first distance is at least 5 mm and the second distance is larger than the first distance. In some instances, the distance between the first and second reception area is at most half of the first distance smaller than the second distance.

In some instances, the light emission area is provided as an active area of the light source provided at the housing. In some instances, the first reception area is provided as an active area of the first photodetector provided at the housing. In some instances, the second reception area is provided as an active area of the second photodetector provided at the housing. In some instances, the third reception area is provided as an active area of the third photodetector provided at the housing. In some instances, the first light emission area is provided as an active area of the first light source provided at the housing, and the second light emission area is provided as an active area of the second light source provided at the housing. In some instances, the light emission area is provided as an end of a light guide provided at the housing, the light guide configured to transmit light from the light source. In some instances, the first and/or second and/or third reception area is provided as an end of a light guide provided at the housing, the light guide configured to transmit light to the first and/or second and/or third photodetector.

In some implementations, the housing is configured to be worn behind the ear of the user. For instance, the hearing device may comprise the housing configured to be worn behind the ear and an additional housing, which may be provided as an earpiece, configured to be at least partially inserted into an ear canal of the ear. Implementing the optical sensor arrangement at a housing wearable behind the ear may offer the advantage of accessing a variety of tissue layers by the light emitted from the light source and detected by the photodetectors that would not be accessible inside the ear canal. Further, a larger area may be available for providing the light emission area and the reception areas at a desired value of the first and second distance, which may offer the advantage of a better choice for an optimized placement of the light emission area and the reception areas, and valuable space inside the ear canal may be saved, which may be useful to implement other functionalities of the hearing device inside the ear canal.

In some instances, the light emission area, the first reception area, and the second reception area are provided at a portion of the housing oriented toward a head of the user when the housing is worn behind the ear of the user. Such a positioning of the optical sensor arrangement may be useful to access not only rather shallow tissue layers, such as skin and/or blood vessels, but also deeper lying tissue such as muscles and/or brain tissue. In some instances, the light emission area, the first reception area, and the second reception area are provided at a face of the housing at which the housing is supported on a top of the ear when the housing is worn behind the ear. Such an arrangement may be useful to provide a better shielding of the optical sensor from ambient light by the ear and/or to ensure a better quality of the sensor signal at a smaller distance to the ear tissue and/or by avoiding other interfering influences at the optical sensor surface such as hair or an eyeglass frame which may also be present behind the ear. In some instances, the light emission area and/or the first reception area and/or the second reception area is configured to be oriented toward the auricularis superior at the ear when the housing is worn behind the ear. Illuminating the ear tissue at the auricularis superior, which is an extrinsic muscle at the ear, by the emitted light and/or detecting the light arriving from the ear tissue at the auricularis superior can offer a particularly large variety of different tissue layers accessible by the optical sensor.

In some implementations, the housing is configured to be at least partially inserted into an ear canal of the ear. Such a housing may be provided as an earpiece at least partially insertable into the ear canal, which may be provided as a single housing, or the hearing device may comprise an additional housing, for instance a housing configured to be worn behind the ear. Implementing the optical sensor arrangement at least partially inside the ear canal may offer the advantage of an improved support of the housing in a stable position by the ear canal wall such that movement artefacts may be less dominant and/or a shielding from ambient light predominantly present outside the ear canal.

In some instances, the light emission area and/or the first reception area and/or the second reception area is configured to be positioned at a bend of a wall of the ear canal when the housing is at least partially inserted into the ear canal. The positioning at the bend may offer a particular efficient shielding of the photodetectors from stray light and may allow access to surrounding ear tissue of good quality such that it can be generally representative for a property of the user's tissue that shall be determined. More particularly, the light emission area and/or the first reception area and/or the second reception area may be configured to be positioned at a protrusion of the ear canal wall at the bend, to enhance these effects. The bend may be a first bend of the ear canal wall, wherein the ear canal wall comprises a second bend located further inside the ear canal. In some instances, at least one of the light emission area, the first reception area, and the second reception area is configured to be positioned at a bend of a wall of the ear canal, and at least one other of the light emission area, the first reception area, and the second reception area is configured to be positioned further inside the ear canal relative to the bend. In some instances, the first reception area and the second reception area are configured to be positioned at the bend when the housing is at least partially inserted into the ear canal. The light source may be also positioned at the bend or further inside the ear canal relative to the bend or further outside the ear canal relative to the bend.

In some instances, the first distance and/or the second distance and/or the third distance extends at least partially around a circumference of the housing. The circumference of the housing may be surrounded by a circumference of the ear canal wall when the housing is at least partially inserted into the ear canal. In some instances, the first distance and/or the second distance and/or the third distance extends at least partially in parallel to a longitudinal axis of the housing along which the housing is at least partially insertable into the ear canal, in particular along a longitudinal axis of the ear canal. In some instances, the first distance and/or the second distance and/or the third distance extends at least partially around the circumference of the housing and at least partially in parallel to the longitudinal axis of the housing, in particular in a transverse direction relative to the circumference and the direction of the longitudinal axis. In this way, the first distance and/or the second distance and/or the third distance may be provided, on the one hand, at a desired value, for instance at a rather big length relative to the distance between the reception areas, and, on the other hand, the light emission and/or reception areas may be provided at the same time at an optimized position for probing the tissue inside the ear canal, for instance at the bend of the ear canal.

FIG. 1 illustrates an exemplary hearing system 100 comprising a hearing device 101. Hearing device 101 comprises a processing unit 104 communicatively coupled to a sensor unit 105 and an output transducer 107 included in a housing 102 configured to be worn at an ear of a user. For example, hearing device 101 may be implemented as a hearing aid configured to provide an amplified version of a detected ambient sound to a user, or a cochlear implant configured to provide electrical stimulation representative of audio content to a user, or a bimodal hearing device configured to provide both amplification and electrical stimulation representative of audio content to a user, or a hearable, such as an earbud or an earphone, configured to reproduce an audio content communicated by a wire or wirelessly to hearing device 101 and/or to reproduce a detected ambient sound with or without altering the ambient sound and/or adding sound features to the ambient sound.

Different types of hearing device 101 can also be distinguished by the position at which they are worn at the ear. Some hearing devices, such as behind-the-ear (BTE) hearing aids and receiver-in-the-canal (RIC) hearing aids, typically comprise a first housing, which may be implemented as an earpiece, configured to be at least partially inserted into an ear canal of the ear, and a second housing configured to be worn at a wearing position outside the ear canal, in particular behind the ear of the user. Sensor unit 105, output transducer 108, and processing unit 104 may then be included in any of the first housing and the second housing, in particular in the same housing or in different housings. Some other hearing devices, as for instance earbuds, earphones, hearables, in-the-ear (ITE) hearing aids, invisible-in-the-canal (IIC) hearing aids, and completely-in-the-canal (CIC) hearing aids, commonly comprise a housing configured to be at least partially inserted inside the ear canal without an additional housing for wearing at the different ear position. Sensor unit 105, output transducer 107, and processing unit 104 may then be included in the single housing, which may be implemented as an earpiece.

Output transducer 107 may be implemented as any suitable audio output device for providing an audio signal to the user, for instance an acoustic transducer configured to generate sound waves when outputting the audio signal, such as a receiver of a hearing aid or a loudspeaker of an earbud, or an audio signal transmitter of a cochlear implant system configured to generate an electric signal for stimulating the user's hearing. Hearing device 101 comprises an audio interface 108 through which the audio signal provided by output transducer 107 can be delivered to the user. Audio interface 108 may be implemented as a sound outlet through which the sound waves generated by output transducer 107 can be delivered into the ear canal of the ear, and/or at least one output electrode of a cochlear implant system by which an electric signal transmitted by output transducer 107 can be outputted to stimulate the user's hearing.

Sensor unit 105 comprises at least one light source configured to provide light, and at least two photodetectors configured to detect a first light intensity and a second light intensity. Sensor unit 105 comprises a sensor interface 106 at housing 102 at which the light provided by the light source can be emitted toward a tissue at the ear, for instance a tissue of the ear and/or a tissue at a part of the head facing the ear, and at which a part of the emitted light which is at least partially scattered inside the tissue can be received in order to be detected by the photodetectors. For instance, sensor interface 106 may include an active area of the light source and/or the photodetectors which may be provided at housing 102, for instance at a surface of the housing. Sensor interface 106 may also be implemented as an aperture in housing 102 and/or a light guide provided at housing 102 through which the light provided by the light source can be emitted and/or the light received at sensor interface 106 can be detected by the photodetectors.

Processing unit 104 can be configured to access data representative of the first light intensity and second light intensity detected by the photodetectors. Processing unit 104 may also be configured to determine a property of the tissue based on the first and second light intensity. Processing unit 104 may also be configured to control the light source to provide the light, for instance to control an intensity and/or wavelength of the provided light and/or a time and/or a time interval during which the light is provided. Processing unit 104 may also be configured to process audio data representative of the audio signal outputted by output transducer 108. Those functionalities may be implemented as a computer program executable by processing unit 104. Hearing device 101 may further comprise a memory configured to store programs executable by processing unit 104 and/or to maintain data controlled by processing unit 104.

Hearing device 101 may include additional components as may serve a particular implementation. For instance, hearing device 101 may further comprise a sound sensor. The sound sensor may be implemented as any suitable audio detection device configured to detect a sound in an ambient environment of the user and/or inside the ear-canal and to provide sound data representative of the detected sound. For instance, the sound sensor may be implemented as a microphone and/or a microphone array and/or a bone conducted sound detector. The sound sensor can be configured to provide audio data comprising information about the detected sound to processing unit 104.

Hearing system 100, as illustrated, may further comprise a communication device 111. Communication device 111 may be implemented, for instance, as a device portable by the user, such as a smartphone or a smartwatch. Communication device 111 comprises a processing unit 114 communicatively coupled to processing unit 104 of hearing device 101. Hearing device 101 may comprise a communication unit 109 configured to establish a communication link with a communication unit 119 implemented in communication device 111. Data may then be communicated between processing units 104, 114 via the communication link. For instance, the communication link may be implemented as a radio frequency (RF) connection. The communicated data may comprise data representative of the first light intensity and second light intensity detected by the photodetectors. Processing unit 104 and/or processing unit 114 may be configured to determine a property of the tissue based on the first and second light intensity. Processing unit 104 and/or processing unit 114 may also be configured to control the light source to provide the light. Communication device 111 may further comprise a memory configured to store programs executable by processing unit 114 and/or to maintain data controlled by processing unit 114. In some instances, the determining of the property of the tissue may be performed jointly by processing unit 104 and processing unit 114, for instance by performing different tasks of the operation. Processing units 104, 114 may be implemented, for instance, as a distributed processing system of processing units 104, 114 and/or in a master/slave configuration of processing units 104, 114.

Figure 2A:
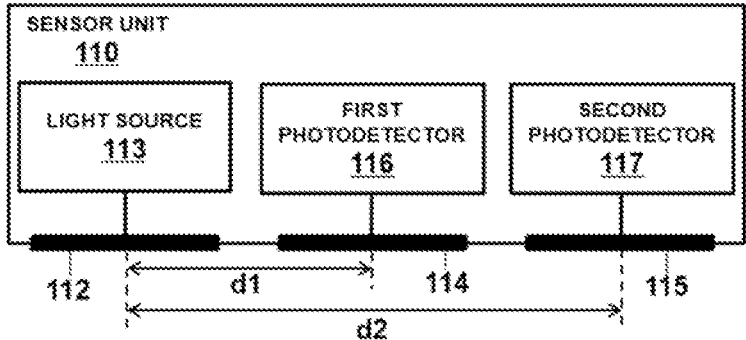
FIGS. 2A-C schematically illustrates some embodiments of the sensor unit of the hearing device illustrated in FIG. 1.

FIG. 2A illustrates an exemplary sensor unit 110 which may be implemented in hearing device 101 as sensor unit 105. Sensor unit 110 comprises a light source 113 configured to provide light emitted from a light emission area 112 at housing 102. When housing 102 is worn at the ear, the light emitted from a light emission area 112 can illuminate an illumination volume extending into tissue at the ear. In some instances, light source 113 comprises light emission area 112. For example, light emission area 112 may correspond to an active area of light source 113 at which the light is emitted from light source 113. Light source 113 may then be provided at housing 102, for instance at a surface of housing 102. In some instances, light emission area 112 can be provided separate from light source 113. For example, sensor unit 110 may comprise a light guide between an active area of light source 113 and light emission area 112. Light emitted from the active area of light source 113 may thus be transmitted to light emission area 112 by the light guide. Light emission area 112 may correspond, for instance, to a free area of the light guide from which light can be emitted. The free area of the light guide may be provided at housing 102, for instance at a surface of housing 102. As another example, light emission area 112 may be provided as an aperture in housing 102. Light emitted from an active area of light source 113 may thus be emitted from housing 102 through the aperture.

Sensor unit 110 further comprises a first photodetector 116 configured to detect a first light intensity of light arriving from a first acceptance volume. When housing 102 is worn at the ear, the first acceptance volume can extend into tissue at the ear. A part of the light emitted at light emission area 112 which is scattered by the tissue into the first acceptance volume can thus contribute to the first light intensity. The first acceptance volume includes a first reception area 114 at housing 102. In some instances, first photodetector 116 comprises first reception area 114. For example, reception area 114 may correspond to an active area of first photodetector 116 at which the light detected. In particular, the light may be absorbed at the active area in order to be converted into an electrical current. First photodetector 116 may then be provided at housing 102, for instance at a surface of housing 102. In some instances, first reception area 114 can be provided separate from first photodetector 116. For example, sensor unit 110 may comprise a light guide between an active area of first photodetector 116 and reception area 114. Light received at reception area 114 may thus be transmitted to the active area of first photodetector 116 by the light guide. Reception area 114 may correspond, for instance, to a free area of the light guide at which light can enter the light guide. The free area of the light guide may be provided at housing 102, for instance at a surface of housing 102. Reception area 114 may also be provided as an aperture in housing 102 through which the light can enter housing 102 to be detected by first photodetector 116 inside. First reception area 114 has a first distance d1 from light emission area 112. First distance d1 may be defined as a distance between a center of light emission area 112 and a center of first reception area 114.

Sensor unit 110 further comprises a second photodetector 117 configured to detect a second light intensity of light arriving from a second acceptance volume. When housing 102 is worn at the ear, the second acceptance volume can extend into tissue at the ear. A part of the light emitted at light emission area 112 which is scattered by the tissue into the second acceptance volume can thus contribute to the second light intensity. The second acceptance volume includes a second reception area 115 at housing 102. In some instances, second photodetector 117 comprises second reception area 115. In some instances, second reception area 115 can be provided separate from second photodetector 117. Second reception area 115 has a second distance d2 from light emission area 112. Second distance d2 may be defined as a distance between a center of light emission area 112 and a center of second reception area 115. Second distance d2 is different from first distance d1. For instance, second reception area 115 may be provided at a larger distance from light emission area 112 than first reception area 114. The difference between first distance d1 and second distance d2 can be selected such that the first light intensity detected by first photodetector 116 and the second light intensity detected by second photodetector 117 contain meaningful information relative to a spatial dependency of the light emitted at light emission area 112 interacting with the tissue when propagating through the tissue.

Figure 2B:
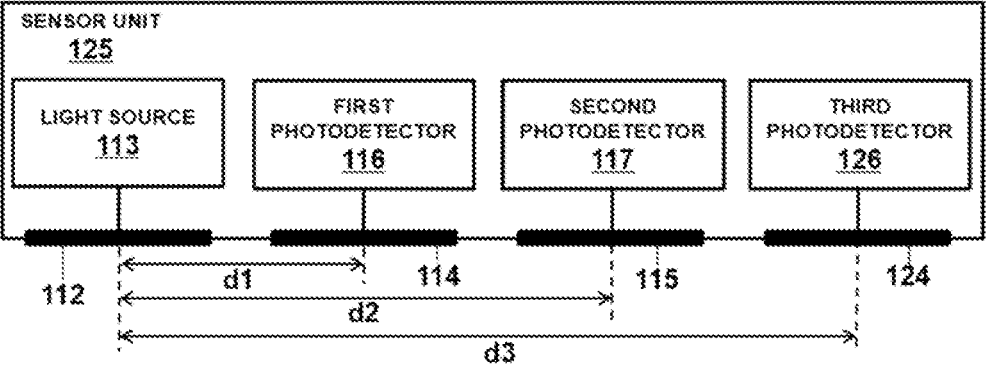

FIG. 2B illustrates an exemplary sensor unit 125 which may be implemented in hearing device 101 as sensor unit 105. Sensor unit 125 further comprises a third photodetector 126 configured to detect a third light intensity of light arriving from a third acceptance volume. When housing 102 is worn at the ear, the third acceptance volume can extend into tissue at the ear. A part of the light emitted at light emission area 112 which is scattered by the tissue into the third acceptance volume can thus contribute to the third light intensity. The second acceptance volume includes a third reception area 124 at housing 102. In some instances, third photodetector 126 comprises third reception area 124. In some instances, third reception area 124 can be provided separate from third photodetector 126. Third reception area 126 has a third distance d3 from light emission area 112. Third distance d3 may be defined as a distance between a center of light emission area 112 and a center of third reception area 124. Third distance d3 is different from first distance d1 and second distance d2. Third distance d3 can be selected such that the third light intensity detected by third photodetector 126 further enhances the information about a spatial dependency of the light interacting with the tissue after emission from light emission area 112.

Information about adjacent tissue compartments, which may include e.g. intravascular and/or extravascular tissue, corresponding, on the one hand, to the difference of the first and second distance d1, d2, and, and on the other hand, to the difference of the second and third distance d2, d3 may thus be obtained. In particular, a monitoring of different penetration depths of the emitted light into the tissue at the different detection distances can thus be realized as the light can be received, on the one hand, at first and second reception areas 114, 115 and detected by photodetectors 116, 117, and on the other hand received at second and third reception areas 115, 124 and detected by photodetectors 117, 126. Those adjacent compartments may be monitored over time, for instance to obtain information about a different water concentration at different times in the adjacent compartments. To illustrate, a diffusion of water and/or glucose from a blood vessel across a capillary wall of the blood vessel into neighboring tissue, and vice versa, may thus be monitored over time. Moreover, an accuracy of the measured spatial dependency and/or a reliability of the measurement may thus be enhanced by providing additional information.

Figure 2C:
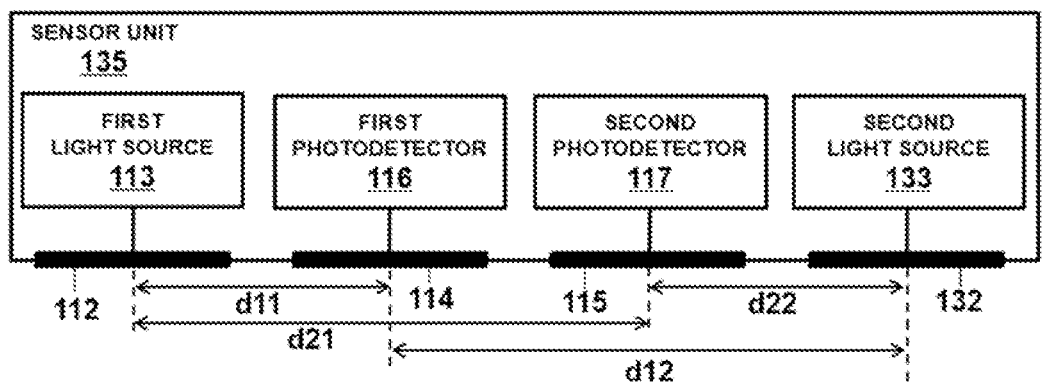

FIG. 2C illustrates an exemplary sensor unit 135 which may be implemented in hearing device 101 as sensor unit 105. Sensor unit 135 comprises first light source 113 configured to provide light emitted from first light emission area 112, and a second light source 133 configured to provide light emitted from a second light emission area 132 at housing 102. When housing 102 is worn at the ear, the light emitted from second light emission area 132 can illuminate an illumination volume extending into tissue at the ear. A center of first light emission area 112 is spaced from a center of second light emission area 132. First light emission area 112 and second light emission area 132 each comprise a portion at which they do not overlap. First light emission area 112 and second light emission area 132 are thus configured to emit light from a different spatial position at housing 102. In some instances, second light source 133 comprises second light emission area 132. In some instances, second light emission area 132 is provided separate from second light source 133. First reception area 114 has a first distance d11 from first light emission area 112. Second reception area 115 has a second distance d21 from first light emission area 112 different from first distance d11. First reception area 114 has a first distance d12 from second light emission area 132. Second reception area 115 has a second distance d22 from second light emission area 132 different from first distance d12.

First distance d12 of first reception area 114 from second light emission area 132 may equal second distance d21 of second reception area 115 from first light emission area 112, and second distance d22 of second reception area 115 from second light emission area 132 may equal first distance d11 of first reception area 114 from first light emission area 112. In this way, a symmetrical arrangement of first and second reception areas 114, 115 relative to first and second light emission areas 112, 132 can be provided. In this arrangement, when light is emitted from first light emission area 112, the light can be received at first and second distances d11 and d21, and when light is emitted from second light emission area 132, the light can be received at the corresponding equal second and first distances d22 and d12.

The symmetrical arrangement can be exploited to eliminate unknown parameters from the measurement results. The unknown parameters may influence each of the measurements when light is emitted from first light emission area 112 and when light is emitted from second light emission area 132 on their own, but may be cancelled out when information obtained by both measurements is taken into account. Those parameters may include, for instance, intrinsic characteristics of light sources 113, 133, for instance an unknown tolerance of the intensity of the emitted light, and/or intrinsic characteristics of photodetectors 116, 117, for instance an unknown tolerance of the detection sensitivity, and/or other unknown characteristics of the optical setup, for instance an unknown coupling efficiency of the light provided by light sources 113, 133 into the tissue at the ear and/or an unknown coupling efficiency of the light received at receptions areas 114, 115 into photodetectors 116, 117. Those parameters can influence the measurement when light is emitted from first light emission area 112 and the measurement when light is emitted from second light emission area 132 in a corresponding way, and may therefore be eliminated based on the information obtained by both measurements. In this way, an individual calibration of sensor 135 prior to the optical measurements, which may involve a rather large effort, could be avoided. Sensor 135 can then be configured to provide the first light intensity detected by first photodetector 116 and the second light intensity detected by second photodetector 117 in a twofold manner, on the one hand based on the light emitted from first light emission area 112 and on the other hand based on the light emitted from second light emission area 132, allowing to evaluate the first light intensity and the second light intensity in a self-calibrated way.

In any of sensor units 115, 125, 135, light source 113, 133 may be configured to provide light at a near infrared (NIR) wavelength, which comprises at least one wavelength between 800 nm and 1650 nm. Photodetectors 116, 117, 126 may be configured to detect the light intensity at that wavelength. The wavelength may correspond to a wavelength of light absorbable by an analyte contained in the tissue at the ear. The analyte may comprise, for instance, water and/or a lipid and/or haemoglobin and/or glucose. For instance, water can absorb light at a wavelength of 970 nm and 1400 nm and 1450 nm and 1500 nm. Haemoglobin can absorb light at a wavelength of 660 nm, which is mainly absorbed by deoxygenated haemoglobin (deoxyhaemoglobin), 880 nm and 940 nm, which is mainly absorbed by haemoglobin saturated with oxygen molecules (oxyhaemoglobin), and 810 nm, which can be absorbed by both deoxyhaemoglobin and oxyhaemoglobin. Lipid can absorb light at a wavelength of 1200 nm. Glucose can absorb light at a wavelength of 1650 nm. An amount of light attenuation at such a wavelength due to light absorption by the analyte may indicate a concentration of the analyte in the tissue. Further, in the case of the wavelength absorbed by haemoglobin, an oxygen saturation index (SpO2) and/or a blood pressure and/or a heart rate may be derived be determining the amount of light attenuation at this wavelength. As another example, in the case of the wavelength absorbed by glucose, a blood sugar level may be determined. The wavelength of the light that can be absorbed by the analyte may also correspond to a peak wavelength of light emitted by light source 113, 133 at a continuous wavelength spectrum and/or a wavelength close to the peak wavelength, for instance a wavelength shifted by at most 50 nm, in some instances at most 20 nm, from the peak wavelength. Light source 113, 133 may be implemented, for instance, as a light emitting diode (LED) and/or a superluminescent diode (SLED) and/or a laser diode (LD). Photodetectors 116, 117, 126 may be implemented, for instance, as a photodiode.

In some instances, light source 113, 133 can be configured to provide light with at least two distinct wavelengths. Photodetectors 116, 117, 126 can then be configured to detect the respective light intensity for each of the at least two distinct wavelengths. Light at the different wavelengths may then be absorbable each by a different analyte contained in the tissue at the ear. In some instances, the wavelengths of the light provided by light source 113, 133 and detectable by photodetectors 116, 117, 126 comprises at least two wavelengths in a wavelength range deviating from one of the following wavelengths by at most 20 nm, in some instances by at most 10 nm: 660 nm, 810 nm, 940 nm, 970 nm, 1000 nm, 1200 nm, 1350 nm, 1400 nm, 1450 nm, 1500 nm, 1550 nm, 1650 nm. In some instances, the wavelengths of the light provided by light source 113, 133 and detectable by photodetectors 116, 117, 126 comprises a first wavelength within a wavelength range deviating from 810 nm by at most 20 nm, and a second wavelength deviating from 970 nm or 1450 nm by at most 20 nm. Thus, a light absorption by the two analytes haemoglobin and water may be probed. In some instances, the wavelengths of the light provided by light source 113, 133 and detectable by photodetectors 116, 117, 126 comprises a first wavelength within a wavelength range deviating from 1200 nm by at most 20 nm, and a second wavelength within a wavelength range deviating from 1400 nm or 1450 nm or 1500 nm by at most 20 nm. Thus, a light absorption by the two analytes lipid and water may be probed. In some instances, the wavelengths of the light provided by light source 113, 133 and detectable by photodetectors 116, 117, 126 comprises a first wavelength within a wavelength range deviating from 1650 nm by at most 50 nm, and a second wavelength within a wavelength range deviating from 1400 nm or 1450 nm or 1500 nm by at most 20 nm. Thus, a light absorption by the two analytes glucose and water may be probed.

In some implementations, light source 113, 133 comprises a first light source element configured to provide the light at the first wavelength of the two distinct wavelengths, and a second light source element configured to provide the light at the second wavelength of the two distinct wavelengths. Light emission area 112, 132 may comprise a first light emission area section at which the light provided at the first wavelength can be emitted, and a second light emission area section at which the light provided at the second wavelength can be emitted. In some instances, the first light emission area section and the second light emission area section are spaced from one another at the housing. First distance d1, d11, d12 of light emission area 112, 132 to first reception area 114 may then be defined separately as a first distance d1, d11, d12 of the first area section of light emission area 112, 132 to first reception area 114, and a first distance d1, d11, d12 of the second area section of light emission area 112, 132 to first reception area 114. Second distance d2, d21, d22 of light emission area 112, 132 to second reception area 115 may then also be defined separately as a second distance d2, d21, d22 of the first area section of light emission area 112, 132 to second reception area 115, and a second distance d2, d21, d22 of the second area section of light emission area 112, 132 to second reception area 115. A light intensity of the light emitted at the two wavelengths from the first and second area section of light emission area 112, 132 can then be detected separately by photodetectors 116, 117 when received at the different distances d1, d2, d11, d12, d21, d22 as defined for each of the two wavelengths. In some instances, the two light source elements of light source 113, 133 can be configured to provide the light at different times such that the light is emitted from the first and second area section of light emission area 112, 132 at different times at the different wavelengths. Thus, the light intensity detected by photodetectors 116, 117 may be resolved at the different times for the different wavelengths.

In some instances, light source 113, 133 may be implemented as a light source array, which may comprise a plurality of spaced light source elements each configured to provide light at one of the at least two distinct wavelengths. For instance, light source 113, 133 may be implemented as an array of LEDs and/or SLEDs and/or LDs. In some instances, light source 113, 133 may be implemented as a broadband light source, which may provide light over a continuous wavelength range including the at least two distinct wavelengths.

In some implementations, photodetector 116, 117, 126 comprises a first photodetector element configured to detect the light at the first wavelength of the two distinct wavelengths, and a second photodetector element configured to detect the light at the second wavelength of the two distinct wavelengths. Reception area 114, 115, 124 may comprise a first reception area section at which the light detectable at the first wavelength can be received at the housing, and a second reception area section at which the light detectable at the second wavelength can be received at the housing. In some instances, the first reception area section and the second reception area section are spaced from one another at the housing. First distance d1, d11, d12 of light emission area 112, 132 to first reception area 114 may then be defined separately as a first distance d1, d11, d12 of light emission area 112, 132 to the first area section of first reception area 114, and a first distance d1, d11, d12 of light emission area 112, 132 to the second area section of first reception area 114. Second distance d2, d21, d22 of light emission area 112, 132 to second reception area 115 may then also be defined separately as a second distance d2, d21, d22 of light emission area 112, 132 to the first area section of second reception area 115, and a second distance d2, d21, d22 of light emission area 112, 132 to the second area section of second reception area 115. A light intensity of the light emitted at light emission area 112, 132 can then be detected separately at the first and second photodetector element of photodetectors 116, 117 when received at the different distances d1, d2, d11, d12, d21, d22 as defined for each of the two wavelengths.

In some instances, photodetectors 116, 117, 126 may each be implemented as a detector array. The detector array may comprise a plurality of spaced photodetector elements each sensitive to one of the at least two distinct wavelengths. Photodetectors 116, 117, 126 may also each be implemented as a single detector configured to detect multiple wavelengths over a wavelength range. Photodetectors 116, 117, 126 may also be provided with a filter configured to separate the at least two distinct wavelengths to be detected by photodetectors 116, 117, 126 from other wavelengths that shall not be detected.

In some instances, light source 113, 133 can be configured to provide light with at least three distinct wavelengths, each separately detectable by photodetectors 116, 117, 126 as a light intensity and each absorbable by a different analyte contained in the tissue at the ear. In some instances, the at least three distinct wavelengths comprise a first wavelength within a wavelength range deviating from 660 nm by at most 20 nm, a second wavelength within a wavelength range deviating from 880 nm or 940 nm by at most 20 nm, and a third wavelength within a wavelength range deviating from 970 nm or 1450 nm by at most 20 nm. Thus, a light absorption by the two analytes haemoglobin, in particular deoxyhaemoglobin and oxyhaemoglobin, and water may be probed. In some instances, the at least three distinct wavelengths comprise a first wavelength within a wavelength range deviating from 810 nm by at most 20 nm, a second wavelength within a wavelength range deviating from 970 nm or 1450 nm by at most 20 nm, and a third wavelength within a wavelength range deviating from 1200 nm by at most 20 nm. Thus, a light absorption by the three analytes haemoglobin, water, and lipid may be probed. In some instances, the at least three distinct wavelengths comprise a first wavelength within a wavelength range deviating from 810 nm by at most 20 nm, a second wavelength within a wavelength range deviating from 970 nm or 1450 nm by at most 20 nm, and a third wavelength within a wavelength range deviating from 1650 nm by at most 50 nm. Thus, a light absorption by the three analytes haemoglobin, water, and glucose may be probed. In some instances, the at least three distinct wavelengths comprise a first wavelength within a wavelength range deviating from 940 nm by at most 20 nm, a second wavelength within a wavelength range deviating from 970 nm by at most 20 nm, and a third wavelength within a wavelength range deviating from 1000 nm by at most 20 nm. Thus, a light absorption peak of water at 970 nm may be resolved. In some instances, the at least three distinct wavelengths comprise a first wavelength within a wavelength range deviating from 1200 nm by at most 50 nm, a second wavelength within a wavelength range deviating from 1450 nm or 1500 nm by at most 50 nm, and a third wavelength within a wavelength range deviating from 1650 nm by at most 50 nm. Thus, a light absorption peak of water at 1450 nm may be resolved. When resolving the respective absorption peak, the light intensities detected at the different wavelengths may be integrated in order to determine a peak area around the absorption peak. An amount of light absorption by the analyte may thus be determined with a higher reliability.

In some implementations, light source 113, 133 comprises a first light source element configured to provide the light at the first wavelength of the three distinct wavelengths, a second light source element configured to provide the light at the second wavelength of the three distinct wavelengths, and a third light source element configured to provide the light at the third wavelength of the three distinct wavelengths. Light emission area 112, 132 may comprise a first light emission area section at which the light provided at the first wavelength can be emitted, a second light emission area section at which the light provided at the second wavelength can be emitted, and a third light emission area section at which the light provided at the third wavelength can be emitted. In some implementations, photodetector 116, 117, 126 comprises a first photodetector element configured to detect the light at the first wavelength of the three distinct wavelengths, a second photodetector element configured to detect the light at the second wavelength of the three distinct wavelengths, and a third photodetector element configured to detect the light at the third wavelength of the three distinct wavelengths. Reception area 114, 115, 124 may comprise a first reception area section at which the light detectable at the first wavelength can be received at the housing, a second reception area section at which the light detectable at the second wavelength can be received at the housing, and a third reception area section at which the light detectable at the third wavelength can be received at the housing.

Figure 3:
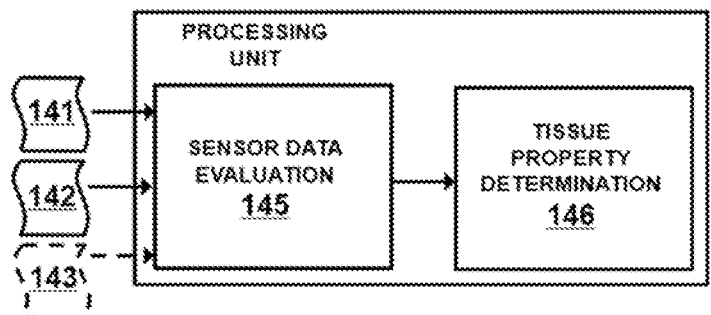
FIG. 3 schematically illustrates different operations that may be performed by the hearing device illustrated in FIG. 1 to determine a property of a tissue at the ear.

FIG. 3 illustrates a functional block diagram of an exemplary sensor data processing algorithm that may be executed by a processing unit 104 of hearing device 101 and/or processing unit 114 of communication device 111. As shown, the algorithm is configured to be applied to first sensor data 141 including the first light intensity detected by first photodetector 116, and to second sensor data 142 including the second light intensity detected by second photodetector 117. In some instances, in which embodiments of sensor unit 125 illustrated in FIG. 2B may be implemented, the algorithm can be configured to be further applied to third sensor data 143 including the third light intensity detected by third photodetector 126. In some instances, in which embodiments of sensor unit 135 illustrated in FIG. 2C may be implemented, first sensor data 141 can include the first light intensity detected by first photodetector 116 at a first time during which light is emitted from first light emission area 112, and at a second time during which light is emitted from second light emission area 132. Second sensor data 142 can include the second light intensity detected by second photodetector 117 at the first time and at the second time. Optionally, third sensor data 143 may also be provided, wherein third reception area 124 and third photodetector 126 may be implemented in sensor unit 135, which may include the third light intensity detected by third photodetector 126 at the first time and at the second time. In some instances, processing unit 104, 114 may be configured to control light sources 113, 133 to provide for the light emitted from first light emission area 112 at the first time, and the light emitted from second light emission area 132 at the second time, for example to switch off second light source 133 during the first time, and to switch off first light source 113 during the second time.

The algorithm comprises a sensor data evaluation module 145, and a tissue property determination module 146. Sensor data evaluation module 145 is configured to evaluate the first light intensity 141 and the second light intensity 142, and optionally also the third light intensity 143, by taking into account a difference between distances d1, d2, d3, d11, d12, d21, d22 at which the detected light has been received. In some instances, in which embodiments of sensor unit 135 illustrated in FIG. 2C may be implemented, sensor data evaluation module 145 is configured to evaluate the first light intensity 141 and the second light intensity 142, and optionally also the third light intensity 143, detected at the first time and at the second time by further taking into account that distances d11, d22 and distances d12, d21 are equal. Tissue property determination module 146 can then determine, based on the evaluation of the detected light intensities, a property of the tissue. The property of the tissue may comprise, for instance, a concentration of an analyte contained in the tissue and/or a hydration index of the tissue and/or a property of blood flowing through the tissue.

Figure 4A:
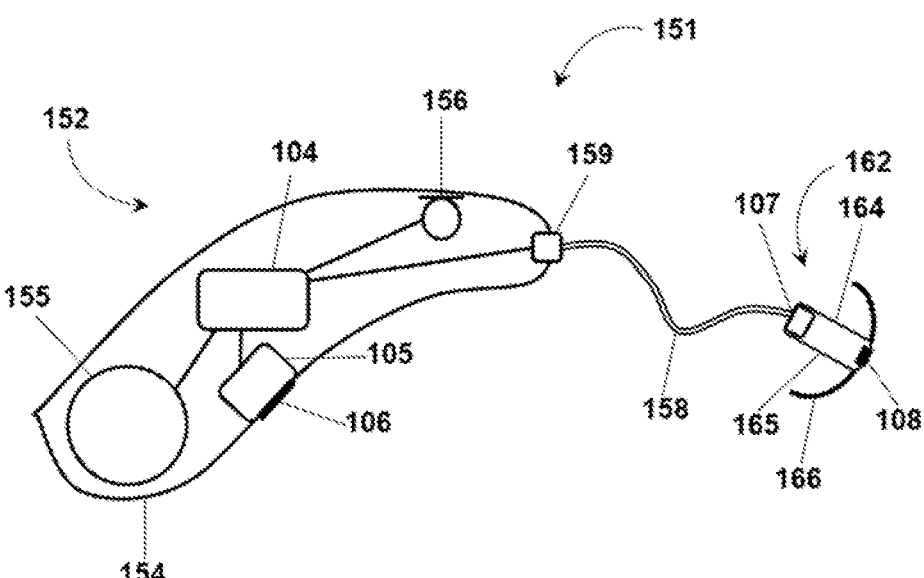
FIG. 4A schematically illustrates some embodiments of the hearing device illustrated in FIG. 1.

FIG. 4A illustrates exemplary implementations of hearing device 101 as a RIC hearing aid 151, in accordance with some embodiments of the present disclosure. RIC hearing aid 151 comprises a BTE part 152 configured to be worn at an ear at a wearing position behind the ear, and an ITE part 162 configured to be worn at the ear at a wearing position at least partially inside an ear canal of the ear. ITE part 162 comprises a housing 164 configured as an earpiece at least partially insertable into the ear canal. Housing 164 comprises a body portion 165 and a sealing member 166 attached to body portion 165. Body portion 165 encloses output transducer 107. Sound outlet 108 may be implemented as an opening at body portion 165 and/or at sealing member 166. Sealing member 166 is adapted to contact an ear canal wall when housing 164 is at least partially inserted into the ear canal. An acoustical seal with the ear canal wall may thus be provided at the housing portion contacting the ear canal wall. The acoustic seal may at least partially block ambient sound from entering the ear canal. Sealing member 166 may be implemented, for instance, as a flexible member adaptable to the ear canal shape, which may have a shape of a dome, or a shell having a shape customized to the shape of an individual ear canal. Housing 164 is a first housing. BTE part 152 comprises a second housing 154 configured to be worn behind the ear. Housing 154 accommodates processing unit 104 communicatively coupled to a sound detector 156 and sensor unit 105. Sensor interface 106 of sensor unit 105 is provided at housing 154. BTE part 152 and ITE part 162 are interconnected by a cable 158. Processing unit 104 is communicatively coupled to output transducer 107 via cable 158 and a cable connector 159 provided at second housing 154. BTE part 152 may further include a battery 155 as a power source for the above described components.

FIG. 4B illustrates exemplary implementations of a housing 171 of hearing device 101 at least partially insertable into an ear canal. For instance, housing 171 may be a housing of an ITE hearing aid, an IIC hearing aid, a CIC hearing aid, an ITE part of a RIC hearing aid, an earbud, an earphone, a hearable, or the like. Housing 171 comprises a body portion 173 enclosing components of hearing device 101, and a sealing member 175 configured to contact a wall of the ear canal. Sealing member 175 is a flexible member configured to conform to a shape of the ear canal. In the illustrated example, body portion 173 has a cylindrical surface 174, and sealing member 175 has a dome shaped surface 176. Sealing member 175 may be attached to body portion 173 at a section of body portion at which a cross section of sealing member 174 matches a cross section of body portion 173. Sealing member 175 projects from body portion 173 such that an empty space 177 is provided between sealing member 175 and body portion 173, at least when housing 171 is removed from the ear canal. When housing 171 is at least partially inserted into the ear canal, sealing member 175 can deform its shape within empty space 177 to conform to the shape of the ear canal. For instance, when housing 171 is at least partially inserted into the ear canal, sealing member 175 may be deformed to be rather close to cylindrical surface 174 of body portion 173 such that empty space 177 is rather small. A sound outlet 179 is provided at a front end of housing 171 facing an inner region of the ear canal when housing 171 is at least partially inserted into the ear canal.

Light emission area 112, first reception area 114, and second reception area 115 are provided at surface 174 of body portion 173. Light source 113 may by provided at surface 174 or accommodated inside body portion 173 to provide light emitted from light emission area 112. Photodetectors 116, 117 may be provided at surface 174 or accommodated inside body portion 173 to detect light received at reception areas 114, 115. In the illustrated example, light emission area 112, first reception area 114, and second reception area 115 are provided at a section of body portion 173 remote from empty space 177 between body portion 173 and sealing member 174. When housing 171 is at least partially inserted into the ear canal, the light emitted from light emission area 112 can thus illuminate an illumination volume extending into tissue at the ear without traversing or being blocked by sealing member 175. Light arriving from tissue at the ear can also be received at reception areas 114, 115 without traversing or being blocked by sealing member 175. In other examples, light emission area 112, first reception area 114, and second reception area 115 can be provided at a section of body portion 173 adjoining empty space 177 between body portion 173 and sealing member 174. Sealing member 174 can then be configured to allow traversing of the light emitted from light emission area 112 to illuminate the illumination volume extending into the tissue, and to allow traversing of the light arriving from tissue to be received at reception areas 114, 115. In some of these examples, sealing member 175 can be formed of a material transparent or translucent to light, in particular at a wavelength of the light provided by light source 113 and detectable by first photodetector 116 and second photodetector 117.

FIG. 4C illustrates another exemplary implementation of a housing 181 of hearing device 101 at least partially insertable into an ear canal. Light emission area 112, first reception area 114, and second reception area 115 are provided at surface 176 of sealing member 175. In some examples, light source 113 may be provided at surface 174 or accommodated inside body portion 173, and photodetectors 116, 117 may be provided at surface 174 or accommodated inside body portion 173 to detect the light. Another light emission area 112, first reception area 114, and second reception area 115 may then be provided at body portion 173, corresponding to the example illustrated in FIG. 4B. When housing 181 is at least partially inserted into the ear canal, at least part of the light emitted from light emission area 112 at body portion 173 may then propagate through empty space 177 and sealing member 175 to be emitted again from light emission area 112 at sealing member 175 in order to illuminate the illumination volume extending into tissue at the ear. Light arriving from tissue at the ear can then be received at reception areas 114, 115 at sealing member 175 which then can at least partially propagate through sealing member 175 and empty space 177 to be received again at reception areas 114, 115 at body portion 173 in order to be detected by photodetectors 116, 117. Either light emission area 112, first reception area 114, and second reception area 115 at sealing member 175 or at body portion 173 may then be taken as a reference to define first distance d1, d11, d12 between light emission area 112 and first reception area 114, and to define second distance d2, d21, d22 between light emission area 112 and second reception area 115.

FIG. 4D illustrates another exemplary implementation of a housing 191 of hearing device 101 at least partially insertable into an ear canal. Housing 191 is provided as a shell having a shape customized to the shape of an individual ear canal. A surface 186 of housing 191 at least partially contacts a wall of the ear canal when housing 191 is at least partially inserted into the ear canal. Housing 191 thus constitutes a sealing member configured to form an acoustic seal with the ear canal wall at least partially blocking ambient sound from entering the ear canal. In the illustrated example, surface 186 comprises a concavely curved portion 185 configured to conform to a protrusion of the ear canal wall into the ear canal, which can be formed at a bend of the ear canal wall. A sound outlet 189 is provided at a front end of housing 191 facing an inner region of the ear canal when housing 191 is at least partially inserted into the ear canal. Light emission area 112, first reception area 114, and second reception area 115 are provided at surface 186 of housing 191. Light source 113 may be provided at surface 186 or accommodated inside housing 191, and photodetectors 116, 117 may be provided at surface 186 or accommodated inside housing 191. In the illustrated example, light emission area 112, first reception area 114 and second reception area 115 are provided at concave curvature 185 of housing 191, more particularly at a middle portion 184 of concavely curved portion 185 configured to contact the ear canal at a middle portion of the protrusion of the ear canal. When housing 191 is at least partially inserted into the ear canal, the light emitted from light emission area 112 can thus illuminate an illumination volume extending into tissue at the ear at the protrusion of the ear canal, and light arriving from tissue at the protrusion of the ear canal can be received at reception areas 114, 115.

FIG. 5A illustrates some positions at which hearing device 101 can be worn at an ear 201 of a user. Ear 201 comprises an upper portion 202 relative to the user's head, also denoted superior auricular ear portion, adjoining an extrinsic ear muscle commonly known as auricularis superior. Ear 201 further comprises a backwards facing portion 203 relative to the user's head, also denoted posterior auricular ear portion, adjoining an extrinsic ear muscle commonly known as auricularis posterior. Ear 201 further comprises a lower portion 205 relative to the user's head, also denoted inferior auricular ear portion. In the illustrated example, hearing device 101 is implemented as RIC hearing aid 151, wherein first housing 164 of ITE part 162 is at least partially inserted into an ear canal of the ear, and second housing 154 of BTE part 152 is worn behind ear 201. When worn behind the ear, second housing 154 has a first portion 192, also denoted superior auricular housing portion, positioned at superior auricular ear portion 202, and a second portion 193, also denoted posterior auricular housing portion, positioned at posterior auricular ear portion 203. A transition area 194 between superior auricular ear portion 202 and posterior auricular ear portion 203 is indicated by a dotted line. Superior auricular housing portion 192 may also be defined as a portion of housing 154 facing the auricularis superior. Posterior auricular housing portion 193 may also be defined as a portion of housing 154 which is not facing the auricularis superior and adjoins superior auricular housing portion 192 at a peripheral zone of the auricularis superior.

FIG. 5B illustrates some further positions at which hearing device 101 can be worn at ear 201. Ear 201 comprises an ear canal 205 in which the hearing device is at least partially inserted. Ear canal 205 is delimited by an ear canal wall 206. Ear canal wall 206 comprises a first bend 207, which is located at a more outer region of ear canal 205, and a second bend 208, which is located at a more inner region of ear canal 205. At first bend 207, ear canal wall 206 forms a concavely curved protrusion 209 in ear canal 205. Protrusion 209 can include auricular cartilage. In the illustrated example, hearing device 101 is implemented a hearing device comprising housing 181. Sealing member 175 is positioned at first bend 207 of ear canal wall 206 such that surface 176 of sealing member 175 contacts protrusion 209. Light emission area 112, first reception area 114, and second reception area 115 can thus also be provided at first bend 207, in particular at the contact of sealing member 175 with protrusion 209.

The positioning of light emission area 112 and/or first reception area 114 and/or second reception area 115 at protrusion 209 can result in an improved quality of the measured data. In particular, an unintentional detection of straylight entering the ear canal from the ambient environment may thus be reduced. At the same time, at least tissue layers near to a surface of the tissue such as skin and blood vessels may be probed more reliably in such a detector arrangement.

Figures 6A, 6B, 6C:
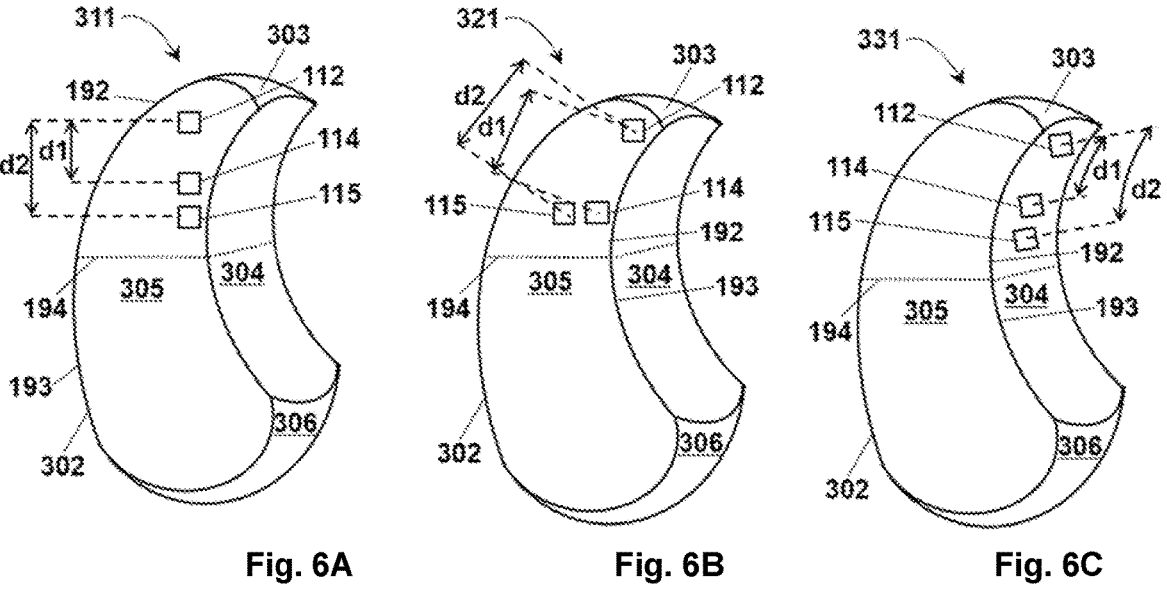
FIGS. 6A-F schematically illustrate some configurations of a housing of the hearing device illustrated in FIG. 1 configured to be worn behind an ear of a user.

FIG. 6A illustrates exemplary implementations of a housing 311 of hearing device 101 configured to be worn behind the ear. For instance, housing 311 may be implemented as housing 154 of BTE part 152 of RIC hearing aid 151. In the illustrated example, light emission area 112, first reception area 114, and second reception area 115 are provided at superior auricular housing portion 192 of housing 311. Such a positioning of the light emission and reception areas 112, 144, 115 can result in an improved quality of the measured data. On the one hand, such a position can allow to access different tissue layers of particular interest in a comprehensive variety, which may include tissue layers near to a surface of the tissue such as skin and blood vessels but also deeper located tissue such as muscular tissue, and even brain tissue. Moreover, such a sensor position can allow to perform the measurement on tissue layers with advantageous properties, as described above. Those tissue layers may also be probed over a sufficiently long distance when the light source and photodetectors are provided at such a sensor position in order to obtain significant measurement results, in particular to also reach deeper located tissue layers such as muscular tissue and/or brain tissue.

Housing 311 comprises an inner lateral surface 305 oriented toward the user's head when housing 311 is worn behind the ear. Any indication relative to the user's head described herein may imply the indication relative to the user's skull and/or tissue surrounding the skull and/or tissue enclosed by the skull. An outer lateral surface may be provided at an opposing side of housing 311 facing away from the user's head when housing 311 is worn. Housing 311 further comprises a bottom surface 304 oriented toward an ear region connecting the ear and the user's head when housing 311 is worn. Bottom surface 304 may thus be at least partially supported on top of the ear, in particular on top of the ear region connected to the head. Housing 311 may further comprise a top surface facing away from the ear region connecting the ear to the head, a front surface 303 oriented toward a front of the head, in particular a viewing direction of the user, and a rear surface 306 oriented toward a rear of the head.

Light emission area 112, first reception area 114, and second reception area 115 are provided at inner lateral surface 305 of housing 311. Light source 113 may be provided at surface 305 or accommodated inside housing 311, and photodetectors 116, 117 may be provided at surface 305 or accommodated inside housing 311. When housing 311 is worn behind the ear, surface 305 faces the user's head, in particular a portion of the head at which the auricularis superior muscle is located. Light emitted from light emission area 112 can thus illuminate, depending on the intensity of the emitted light, an illumination volume which may extend into the auricularis superior and/or be scattered into the auricularis superior, and which may also extend beyond such that it could also reach into brain tissue and/or be scattered into the brain tissue. Similarly, reception areas 114, 115 can thus be positioned such that light arriving from the portion of the head at which the auricularis superior muscle is located can be received to be detected by photodetectors 116, 117, which may include light coming from the auricularis superior and/or even from deeper tissue such as brain tissue. In this way, tissue layers closer to a surface of the tissue such as skin and blood vessels and/or deeper tissue layers such as muscular tissue or brain tissue may be probed by the sensor arrangement.

First distance d1 between first reception area 114 and light emission area 112 is different from second distance d2 between second reception area 115 and light emission area 112. In particular, first distance d1 may be smaller than second distance d2, or vice versa. A distance between first reception area 114 and second reception area 115 may be smaller than first distance d1 and second distance d2. First reception area 114 and second reception area 115 may thus be spaced apart rather closely as compared to their spacing relative to light emission area 112. A difference between first distance d1 and second distance d2 may thus also be smaller than first distance d1 and second distance d2.

The rather small spacing between first reception area 114 and second reception area 115 can ensure rather equivalent conditions for which the light is received. The equivalent conditions may include comparable intrinsic properties of the tissue from which light is received at first reception area 114 and second reception area 115, and undistorted properties of the detected light which may arise when light is detected at different locations, e.g. depending on an anisotropic emission of the light emitted at light emission area 112, a different impact of extraneous light at different locations, or a cross-talk between reception areas 114, 115. In particular, common effects of topical interferents, such as skin nonuniformity, sweat or lotion on the skin, may thus be cancelled. Moreover, a cross talk between light emission area 112 and reception areas 114, 115, e.g. by light reflected from a tissue layer near to a surface of the tissue, can thus be effectively avoided and the detected light can significantly represent the portion of the emitted light after travelling a desired pathlength through the tissue. The rather small spacing between first reception area 114 and second reception area 115 as compared to distances d1, d2 may also allow an improved spatial resolution of the measured data. For instance, a gradient between light received at first reception area 114 and light received at second reception area 115 may be less steep and therefore more informative the smaller the spacing between first reception area 114 and second reception area 115 relative to distances d1, d2 is provided. The rather large distances d1, d2 of reception areas 114, 115 to light emission area 112 can further be employed to increase the detection of light with a rather large penetration depth into the tissue. In particular, the larger distances d1, d2, the longer the detected light can propagate inside the tissue after the light is emitted from light emission area 112, and therefore may also reach into rather deep tissue layers. In some implementations, a distance between first reception area 114 and second reception area 115 may thus be minimized, and distances d1, d2 from light emission area 112 may be maximized and/or selected according to a desired penetration depth of the detected light in order to target a desired layer of the probed tissue.

Providing light emission and reception areas 112, 114, 115 at housing 311 wearable behind the ear can offer the advantage of rather large surfaces 304, 305 on which the distance between reception areas 114, 115, and distances d1, d2 from light emission area 112 can be selected to conform with those requirements. In some implementations, the distance between first reception area 114 and second reception area 115 may be selected to be at least two times smaller as compared to the smaller distance of first distance d1 and second distance d2. In some implementations, the distance between first reception area 114 and second reception area 115 may be selected to be at least three times smaller as compared to the smaller distance of first distance d1 and second distance d2. In some instances, the smaller distance of first distance d1 and second distance d2 is at least 5 mm, and the distance between reception areas 114, 115 is at most half of this distance, in particular one third of this distance. For example, first distance d1 may have a value of about 6 mm, and second distance d2 may have a value of about 8 mm. Such an arrangement can be suitable to not only probe the tissue layers in proximity to a surface of the tissue, but also deeper tissue layers. An even deeper penetration depth may be achieved by further increasing both first distance d1 and second distance d2, wherein the distance between reception areas 114, 115 may be kept equal.

In the illustrated example, first distance d1 and second distance d2 extend in the same direction. Correspondingly, light emission area 112, first reception area 114, and second reception area 115 are arranged along a geodesic line on surface 305. In particular, as illustrated, surface 305 may be substantially flat. Light emission and reception areas 112, 114, 115 may thus be strung together at distances d1, d2 on a straight line on surface 305. Second reception area 115 is located behind first reception area 114 relative to light emission area 112.

FIG. 6B illustrates exemplary implementations of another housing 321 of hearing device 101 configured to be worn behind the ear. As illustrated, distances d1, d2 extend in different directions. Light emission area 112, first reception area 114, and second reception area 115 are positioned in a triangular arrangement on surface 305. Second reception area 115 is located next to first reception area 114 relative to light emission area 112. Such an arrangement may be employed to reduce the difference between distances d1, d2 by keeping the shorter distance of first distance d1 and second distance d2 at a desired value. In some instances, the difference between distances d1, d2 may be minimized by arranging light emission and reception areas 112, 114, 115 at corners of a rectangular triangle. The distance between reception areas 114, 115 may also be kept rater small, in particular by arranging reception areas 114, 115 next to each other, and, at the same time, distances d1, d2 may be kept rather large. Reducing or minimizing the difference between distances d1, d2 may be employed for improving a spatial resolution of the measured data, in particular for reducing a gradient between the light received at first reception area 114 and the light received at second reception area 115.

FIG. 6C illustrates exemplary implementations of another housing 331 of hearing device 101 configured to be worn behind the ear. Light emission and reception areas 112, 114, 115 are provided at bottom surface 304. Bottom surface 304 is curved to conform to the ear region connecting the ear and the user's head when housing 331 is worn. In the illustrated example, distances d1, d2 extend in an equal direction on surface 304, corresponding to the arrangement of light emission and reception areas 112, 114, 115 at housing 311 illustrated in FIG. 6A. In some other instances, distances d1, d2 can extend in different directions on surface 304, corresponding to the arrangement of light emission and reception areas 112, 114, 115 at housing 321 illustrated in FIG. 6B, in particular to achieve a corresponding benefit by reducing or minimizing the difference between distances d1, d2. When housing 331 is worn behind the ear, surface 304 faces an ear region connecting the ear and the user's head user's from above the ear region. Light emitted from light emission area 112 can thus illuminate an illumination volume extending into tissue at the ear from above. Reception areas 114, 115 are positioned such that light arriving from the ear region below can be received and detected by photodetectors 116, 117. Such an arrangement may offer the advantage of an improved shielding of ambient light by the ear region below which is contacted by housing 331 at surface 304. A disadvantage may be, however, that tissue other than ear tissue, which may include skin, cartilage, and blood vessels, may not be accessible.

Figures 6D, 6E, 6F:
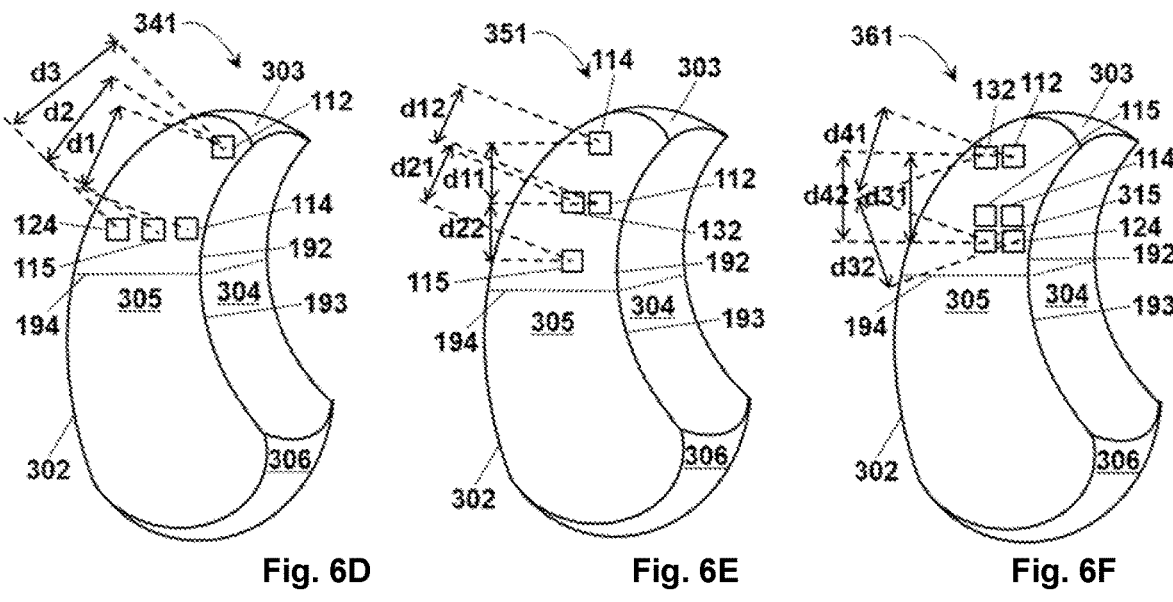

FIG. 6D illustrates exemplary implementations of another housing 341 of hearing device 101 configured to be worn behind the ear. Sensor unit 125, as illustrated in FIG. 2B, may be implemented correspondingly by providing third reception area 124 at housing 341, for instance at bottom surface 304 or at inner lateral surface 305, as illustrated in FIG. 6D. Third photodetector 126 may be provided at surface 304, 305 of housing 341 or accommodated inside housing 341. In the illustrated example, first distance d1, second distance d2, and third distance d3 extend in different directions. Thus a corresponding effect as described above in conjunction with housing 321, 331 illustrated in FIGS. 6B, C may be achieved. In the illustrated example, reception areas 114, 115, 124 are arranged next to each other in a line. Light intensities detected at different distances d1, d2, on the one hand, and light intensities detected at different distances d2, d3, on the other hand, can thus be employed to obtain information about adjacent tissue compartments, as described in conjunction with FIG. 2B.

FIG. 6E illustrates exemplary implementations of another housing 351 of hearing device 101 configured to be worn behind the ear. Sensor unit 135, as illustrated in FIG. 2C, may be implemented correspondingly by providing second light emission area 132 at housing 351, for instance at bottom surface 304 or at inner lateral surface 305, as illustrated in FIG. 6E. Second light source 133 may be provided at surface 304, 305 of housing 351 or accommodated inside housing 351. In the illustrated example, reception areas 114, 115 are arranged next to each other in between first light emission area 112 and second light emission area 132. Light emission areas 112, 132 are positioned on opposing sides relative to a line along which reception areas 114, 115 are arranged. The position of first light emission area 112 is shifted from the position of second light emission area 132 in a direction in which the line along which reception areas 114, 115 are arranged extends. In this way, first distance d11 of first reception area 114 from first light emission area 112 can be provided equal to second distance d22 of second reception area 115 from second light emission area 132, and second distance d21 of second reception area 115 from first light emission area 112 can be provided equal to first distance d12 of first reception area 114 from second light emission area 132. The symmetrical arrangement can be exploited to eliminate unknown parameters from the measurement results, as described in conjunction with FIG. 2C. Moreover, each of equal distances d11, d22 can be provided to extend in a different direction at housing 351 as compared to each of equal distances d12, d21. Thus, the difference between each of equal distances d12, d21 and each of equal distances d11, d22 can be reduced or minimized, as described above.

FIG. 6F illustrates exemplary implementations of another housing 361 of hearing device 101 configured to be worn behind the ear. In these implementations, advantages of sensor unit 125, as illustrated in FIG. 2B, and sensor unit 135, as illustrated in FIG. 2C, may be combined by providing second light emission area 132 and third reception area 124 at housing 361, for instance at bottom surface 304 or at inner lateral surface 305, as illustrated in FIG. 6F. In addition, a fourth reception area 315 may be provided at housing 361. A fourth photodetector may be provided at surface 304, 305 of housing 361 or accommodated inside housing 341. In the illustrated example, third reception area 124 and fourth reception area 315 are arranged next to each in a line extending in parallel to a line along which first reception area 114 and second reception area 115 are arranged. A distance between third and fourth reception areas 124, 315 equals the distance between first and second reception areas 114, 115. A distance between third and first reception areas 124, 114 equals the distance between second and fourth reception areas 114, 305. For instance, reception areas 114, 115, 124, 315 may be positioned in a rectangular arrangement. The distance between third and first reception areas 124, 114 and the distance between second and fourth reception areas 114, 305 may also equal the distance between third and fourth reception areas 124, 315 and the distance between first and second reception areas 114, 115. For instance, reception areas 114, 115, 124, 315 may be positioned at the corners of a square.

The position of first light emission area 112 is shifted from the position of second light emission area 132 in a direction of extension of the line in which reception areas 114, 115 are arranged. In the illustrated example, light emission areas 112, 132 are positioned on the same side relative to a line along which reception areas 114, 115 are arranged. In this way, first distances d11, d12 of first reception area 114 from first and second light emission area 112, 132, and second distances d21, d22 of second reception area 115 from first and second light emission area 112, 132 can be provided corresponding to the arrangement illustrated in FIG. 6E, wherein distances d11 and d22 are equal, and distances d12 and d21 are equal. First light emission area 112 and first and third reception areas 114, 124 may be arranged in a first line, and second light emission area 132 and second and fourth reception areas 115, 315 may be arranged in a second line in parallel to the first line. Thus, a rectangular arrangement of light emission and reception areas 112, 114, 115, 124, 132, 315 may be provided.

A third distance d31 of third reception area 124 from first light source 112 may then be larger than first distance d11 of first reception area 114 from first light source 112. A third distance d32 of third reception area 124 from second light source 132 may be larger than first distance d12 of first reception area 114 from second light source 132. A fourth distance d41 of fourth reception area 315 from first light source 112 may be larger than second distance d21 of second reception area 115 from first light source 112. A fourth distance d42 of fourth reception area 315 from second light source 132 may be larger than second distance d22 of second reception area 114 from second light source 132. Third distance d31 of third reception area 124 from first light emission area 112 can be provided equal to fourth distance d42 of fourth reception area 315 from second light emission area 132, and fourth distance d41 of fourth reception area 315 from first light emission area 112 can be provided equal to third distance d32 of third reception area 124 from second light emission area 132. Equal distances d31, d42 can then also be provided to extend in different directions at housing 361 as compared to equal distances d32, d41.

Housing 361 illustrated in FIG. 6F can be employed in some implementations of sensor unit 125 illustrated in FIG. 2B, and some implementations of sensor unit 135 illustrated in FIG. 2C. The symmetrical arrangement of light emission and reception areas 112, 114, 115, 124, 132, 315 can be exploited to eliminate unknown parameters from the measurement results, as described in conjunction with FIG. 2C. Light intensities detected at different distances d11, d12, d21, d22, on the one hand, and light intensities detected at different distances d31, d32, d41, d42, on the other hand, can be employed to obtain information about adjacent tissue compartments, as described in conjunction with FIG. 2B. In particular, the light may be emitted at at least two different wavelengths from each light emission area 112, 132, which may be absorbable by two different analytes contained in the tissue compartments, and received at the at least two different wavelengths at each reception area 114, 115, 124, 315.

Housing 361 illustrated in FIG. 6F can also be employed in some implementations of sensor unit 110 illustrated in FIG. 2A. In these implementations, light source 113 of sensor unit 110 may comprise two light source elements each providing light at one of two distinct wavelengths. Each wavelength may be absorbable by a different analyte contained in the tissue. Light emission area 112 of sensor unit 110 illustrated in FIG. 2A may then be implemented as two light emission area sections, each light emission area section emitting light with a different wavelength from the two distinct wavelengths. Those light emission area sections can be provided as the light emission areas 112, 132 on housing 361 illustrated in FIG. 6F. Light provided at a first wavelength by the first light source element of light source 113 may then be emitted at first light emission area section 112. Light provided at a second wavelength by the second light source element of light source 113 may then be emitted at second light emission area section 132.

First photodetector 116 of sensor unit 110 illustrated in FIG. 2A may comprise two photodetector elements each configured to detect light at one of the distinct wavelengths of the light provided by light source 113. First reception area 114 of sensor unit 110 illustrated in FIG. 2A may then be implemented as two reception area sections which can be provided as the reception areas 114, 115 on housing 361 illustrated in FIG. 6F. Light detected at a first wavelength by the first photodetector element of first photodetector 116 may then be received at reception area section 114 associated with the first photodetector element. Light detected at a second wavelength by the second photodetector element of first photodetector 116 may then be received at reception area section 115 associated with the second photodetector element. Light emitted at the first wavelength from first light emission area 112 can thus be received at a distance d1 from first light emission area 112 at reception area section 114 associated with the first photodetector element. Light emitted at the second wavelength from second light emission area 132 can thus be received at a distance d1 from second light emission area 132 at reception area section 115 associated with the second photodetector element.

Second photodetector 117 of sensor unit 110 illustrated in FIG. 2A may also comprise two photodetector elements each configured to detect light at one of the distinct wavelengths of the light provided by light source 113. Second reception area 115 of sensor unit 110 illustrated in FIG. 2A may then be implemented as two reception area sections which can be provided as reception areas 124, 315 on housing 361 illustrated in FIG. 6F. Light detected at a first wavelength by the first photodetector element of second photodetector 117 may then be received at reception area section 124 associated with the first photodetector element. Light detected at a second wavelength by the second photodetector element of second photodetector 117 may then be received at reception area section 315 associated with the second photodetector element. Light emitted at the first wavelength from first light emission area 112 can thus be received at a distance d2 from first light emission area 112 at reception area section 124 associated with the first photodetector element. Light emitted at the second wavelength from second light emission area 132 can thus be received at a distance d2 from second light emission area 132 at reception area section 315 associated with the second photodetector element.

In this way, in some implementations of sensor unit 110 illustrated in FIG. 2A, a light intensity of the light emitted at the two wavelengths from light emission area sections 112, 132 can be detected separately by the first and second photodetector element of photodetectors 116, 117 when received at the different distances d1, d2 for each of the two wavelengths.

FIG. 7A illustrates exemplary implementations of a housing 411 of hearing device 101 configured to be inserted at least partially inside the ear canal. For instance, housing 411 may be implemented as any of housings 171, 181, 191 illustrated in FIGS. 4B-D. A surface of housings 171, 181, 191 is schematically indicated in FIG. 7A as a cylindrical surface 404 of housing 411. A central axis 405 of housing 171, 181, 191, 411 extends in a direction in which housing 171, 181, 191, 411 is insertable into the ear canal. When housing 411 is inserted into the ear canal, central axis 405 may correspond to a central axis of the ear canal. A circumference 406 of housing 171, 181, 191, 411 may correspond to a geodesic line extending around central axis 405 on surface 404. In the schematic illustration in FIG. 7A, circumference 406 of surface 404 is indicated rather large as compared to a length of surface 404 in parallel to central axis 405. In real implementations, as illustrated in FIGS. 4B-D by housings 171, 181, 191, a length of surface 404 in the direction of central axis 405 is usually larger. FIG. 7A may thus only represent a slice of housing 411 extending over a portion of a length of housing, for instance a slice of housing 411 at least partially contacting the ear canal wall after insertion of housing 411.

A specific position of circumference 406 on surface 404 relative to the direction of extension of central axis 405 is indicated in FIG. 7A as a dotted line extending around surface 404. In some implementations, the specific position of circumference 406 relative to the direction of extension of central axis 405 may correspond to a position at which surface 404 contacts the wall of the ear canal when housing 411 is inserted into the ear canal. At least a region of surface 404 adjacent to the specific position of circumference 406 may also contact the wall of the ear canal after insertion of housing 411. For instance, the specific position of circumference 406 can be provided on surface 176 of sealing member 175 illustrated in FIGS. 4B, C, or on surface 186 of shell 191 illustrated in FIG. 4D. The specific position of circumference 406 may also be provided on surface 174 of body portion 173 illustrated in FIGS. 4B, C, which may not contact the ear canal wall.

In some implementations, the specific position of circumference 406 relative to the direction of extension of central axis 405 may correspond to a position at which the ear canal wall comprises first bend 207, as illustrated in FIG. 5B, or a position close to first bend 207 of the ear canal wall, for instance at most 5 mm distant from first bend 207. In some instances, the specific position of circumference 406 may contact the ear canal wall at first bend 207 or close to first bend 207. In some instances, the specific position of circumference 406 relative to the direction of extension of central axis 405 may correspond to a position at which the ear canal wall comprises protrusion 209 at first bend 207. In particular, the specific position of circumference 406 may contact the ear canal wall at protrusion 209.

Light emission and reception areas 112, 114, 115 are provided at surface 404 of housing 404. Light source 113 may be provided at surface 404 or accommodated inside housing 411, and photodetectors 116, 117 may be provided at surface 404 or accommodated inside housing 411. When housing 411 is at least partially inserted into the ear canal, surface 404 faces a wall of the ear canal. In some instances, surface 404 contacts the ear canal wall at the position of light emission and reception areas 112, 114, 115. In some instances, surface 404 may have a distance from the ear canal wall at the position of light emission and reception areas 112, 114, 115. Light emitted from light emission area 112 can thus illuminate an illumination volume extending into tissue at the ear canal wall, and reception areas 114, 115 can receive light arriving from tissue at the ear canal wall to be detected by photodetectors 116, 117. In this way, at least information from tissue layers near to a surface of the tissue at the ear canal may be collected by the light detected by photodetectors 116, 117. In the illustrated example, light emission and reception areas 112, 114, 115 are arranged along circumference 404. First distance d1 and second distance d2 thus extend along circumference 404. In particular, light emission and reception areas 112, 114, 115 can be arranged at the specific position of circumference 406 relative to the direction of extension of central axis 405. The specific position may be provided at first bend 207 of the ear canal wall and/or at protrusion 209 at first bend 207. This can have the advantage to shield the sensor arrangement from ambient stray light by first bend 207 and/or protrusion 209. Moreover, the tissue layers at protrusion 209 and/or the tissue layers extending from protrusion 209 further inside the user's head can be sufficiently expansive in order to be representative of a physical property of the user which can thus be probed.

FIG. 7B illustrates exemplary implementations of another housing 421 of hearing device 101 configured to be inserted at least partially inside the ear canal. As illustrated, reception areas 114, 115 are arranged along circumference 406. Light emission area 112 is provided at a position at surface 404 which is shifted from the position at which reception areas 114, 115 are provided in the direction of central axis 405. First distance d1 and second distance d2 thus both extend in a direction including a directional component of central axis 405. First distance d1 and second distance d2 extend in different directions at surface 404. For instance, light emission area 112 may be spaced from first reception area 114 in parallel to central axis 405 such that first distance d1 extends in parallel to central axis 405. Second distance d2 then extends in a transverse direction relative to central axis 405. The specific position of circumference 406 may be provided for such that, when housing 421 is at least partially inserted into the ear canal, the specific position is positioned at first bend 207 of the ear canal wall and/or at protrusion 209 at first bend 207. In some instances, light emission area 112 may be positioned to be located further inside the ear canal as compared to the specific position of circumference 406. In some instances, light emission area 112 may be positioned to be located further toward an entrance of the ear canal.

FIG. 7C illustrates exemplary implementations of another housing 431 of hearing device 101 configured to be inserted at least partially inside the ear canal. Sensor unit 125, as illustrated in FIG. 2B, may be implemented correspondingly by providing third reception area 124 at surface 404 of housing 431, as illustrated in FIG. 7C. Third photodetector 126 may be provided at surface 404 of housing 431 or accommodated inside housing 431. In the illustrated example, reception areas 114, 115, 124 are arranged next to each other in a line extending in parallel to central axis 405 or in a transverse direction relative to central axis 405. The position of light emission area 112 on surface 404 is shifted relative to the axial arrangement of reception areas 114, 115, 124 in a circumferential direction of surface 404. Distances d1, d2, d3 thus extend in different directions on surface 404. In some instances, one of reception areas 114, 115, 124 is located at the specific position of circumference 406 which may be positioned at protrusion 209 and/or at first bend 207 of the ear canal wall when housing 431 is at least partially inserted. In some instances, the other two of reception areas 114, 115, 124 may also be located at protrusion 209 and/or at first bend 207, or close to protrusion 209 and/or first bend 207. In some instances, the other two of reception areas 114, 115, 124 may be located closer to an inner region of the ear canal as compared to the reception area located at the specific position of circumference 406. In some instances, light emission area 112 is also located at the specific position of circumference 406.

FIG. 7D illustrates exemplary implementations of another housing 441 of hearing device 101 configured to be inserted at least partially inside the ear canal. Sensor unit 135, as illustrated in FIG. 2C, may be implemented correspondingly by providing second light emission area 132 at surface 404 of housing 441, as illustrated in FIG. 7D. Second light source 133 may be provided at surface 404 of housing 441 or accommodated inside housing 441. In the illustrated example, light emission and reception areas 112, 114, 115, 132 are arranged along circumference 404. First distance d11 of first reception area 114 from first light emission area 112 is equal to second distance d22 of second reception area 115 from second light emission area 132, and second distance d21 of second reception area 115 from first light emission area 112 is equal to first distance d12 of first reception area 114 from second light emission area 132. Distances d11, d12, d21, d22 extend along circumference 404, which may be located at the specific position relative to the direction of extension of central axis 405, as described above. In the illustrated example, light emission areas 112, 132 are positioned between reception areas 114, 115. In other instances, reception areas 114, 115 are positioned between light emission areas 112, 132.

FIG. 7E illustrates exemplary implementations of another housing 451 of hearing device 101 configured to be inserted at least partially inside the ear canal. Reception areas 114, 115 are positioned along a first line extending on surface 404, and light emission areas 112, 132 are positioned along a second line on surface 404 in parallel to first line. In the illustrated example, the first line and the second line extend in parallel to central axis 404. In other instances, the first line and the second line extend in a transverse direction relative to central axis 404. Light emission areas 112, 132 are thus shifted relative to reception areas 114, 115 in a circumferential direction of housing 451. In the illustrated example, a distance between light emission areas 112, 132 is smaller than the distance between reception areas 114, 115. Light emission areas 112, 132 may be positioned in proximity to each other, and reception areas 114, 115 may be positioned further spaced from each other, for instance by at least twice the distance between reception areas 114, 115. Light emission and reception areas 112, 114, 115, 132 can thus each provided at a different position relative to central axis 405. In this way, a length of surface 451 along central axis 405, which may be larger than circumference 406, may be exploited to distribute light emission and reception areas 112, 114, 115, 132 on surface 451 in an advantageous manner, in particular to ensure a desired minimum distance between light emission areas 112, 132 and reception areas 114, 115. In other instances, the distance between light emission areas 112, 132 can be larger than the distance between reception areas 114, 115, or equal to the distance between reception areas 114, 115.

Distances d11, d22 are equal to each other, and distances d12, d21 are equal to each other. Each of equal distances extends in a different direction on surface 404 of housing 351 than each of equal distances d12, d21. In particular, in the illustrated example, all distances d11, d12, d21, d22 between light emission areas 112, 132 and reception areas 114, 115 extend in different directions. Further, in the illustrated example, second reception area 115 is located at the specific position of circumference 406, which may correspond to the position of first bend 207 of the ear canal wall and/or at protrusion 209 at first bend 207 when housing 451 is at least partially inserted. First reception area 114 may then be located further inside the ear canal to improve a shielding of first reception area 114 from extraneous light entering the ear canal.

FIG. 7F illustrates exemplary implementations of another housing 461 of hearing device 101 configured to be inserted at least partially inside the ear canal. Light emission and reception areas 112, 114, 115, 132 are all positioned on a line on surface 404 extending in a transverse direction relative to central axis 405 and circumference 406. Light emission and reception areas 112, 114, 115, 132 can thus each be provided at a different position relative to central axis 405 and a different position relative to circumference 406. In the illustrated example, reception areas 114, 115 are positioned between light emission areas 112, 132. In other examples, light emission areas 112, 132 can be positioned between reception areas 114, 115.

Housing 461 illustrated in FIG. 7F can thus be employed in some implementations of sensor unit 135 illustrated in FIG. 2C, wherein the symmetrical arrangement of light emission and reception areas 112, 114, 115, 132 can be exploited to eliminate unknown parameters from the measurement results.

Housing 461 illustrated in FIG. 7F can also be employed in some implementations of sensor unit 110 illustrated in FIG. 2A. In these implementations, light source 113 of sensor unit 110 may comprise two light source elements each providing light at one of two distinct wavelengths. Light emission area 112 of sensor unit 110 illustrated in FIG. 2A may then be implemented as two light emission area sections, each light emission area section emitting light with a different wavelength from the two distinct wavelengths. Those light emission area sections can be provided as the light emission areas 112, 132 on housing 461 illustrated in FIG. 7F. Light provided at a first wavelength by the first light source element of light source 113 may then be emitted at first light emission area section 112. Light provided at a second wavelength by the second light source element of light source 113 may then be emitted at second light emission area section 132.

Photodetectors 116, 117 of sensor unit 110 can each be configured to detect the light at the two distinct wavelengths. Light emitted at the first wavelength from first light emission area section 112 can thus be received at a distance d1 from first light emission area 112 section at first reception area 114, corresponding to distance d11 illustrated in FIG. 7F, to be detected by first photodetector 116. Light emitted at the first wavelength from first light emission area section 112 can be received at a distance d2 from first light emission area section 112 at second reception area 115, corresponding to distance d21 illustrated in FIG. 7F, to be detected by second photodetector 117. Light emitted at the second wavelength from second light emission area section 132 can be received at a distance d1 from second light emission area section 132 at second reception area 115, corresponding to distance d22 illustrated in FIG. 7F, to be detected by second photodetector 117. Light emitted at the second wavelength from second light emission area section 132 can be received at a distance d2 from second light emission area section 132 at first reception area 114, corresponding to distance d21 illustrated in FIG. 7F, to be detected by first photodetector 116.

In this way, a light intensity of the light emitted at the two wavelengths from light emission area sections 112, 132 can be detected separately by photodetectors 116, 117 when received at the different distances d1, d2 for each of the two wavelengths. In some instances, the two light source elements of light source 113 can be configured to provide the light at different times such that the light is emitted from light emission area sections 112, 132 at different times at the different wavelengths. Thus, the light intensity detected by photodetectors 116, 117 may be resolved at the different times for the different wavelengths.

Figure 8A:
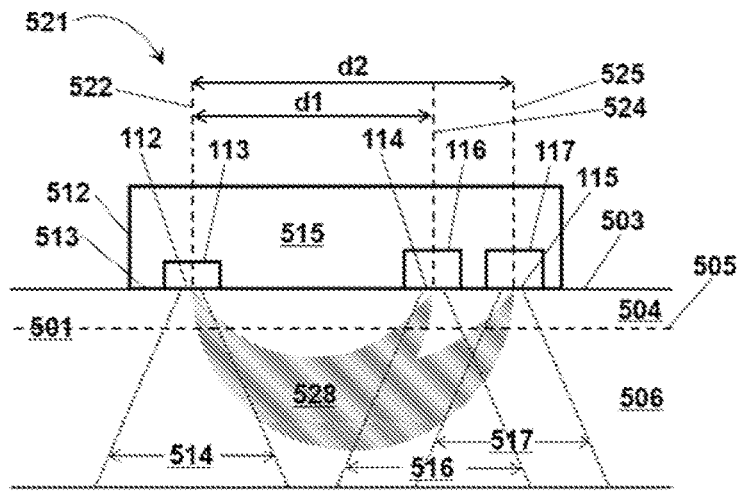
FIGS. 8A-G schematically illustrate some configurations of measurements performed on a tissue at the ear when some embodiments of the hearing device illustrated in FIG. 1 are worn at the ear.

FIG. 8A illustrates a measurement arrangement 521 in which a housing 512 of hearing device 101 is worn at an ear such that housing 512 is positioned at a tissue 501 at the ear. Tissue 501 comprises at least one outer tissue layer 504, and at least one inner tissue layer 506. A transition 505 between outer tissue layer 504 and inner tissue layer 506 may be gradual. In some instances, outer tissue layer 504 and inner tissue layer 506 are provided as a tissue rather close to a surface 503 of tissue 501 at outer tissue layer 504. For example, outer tissue layer 504 may comprise at least one skin layer, and inner tissue layer 506 may comprise at least one layer of subcutaneous tissue including blood vessels. In some instances, outer tissue layer 504 is provided as at least one tissue layer close to surface 503 of tissue 501, which may include skin and blood vessels, and inner tissue layer 506 is provided as at least one deeper located tissue layer, which may include muscular tissue and/or brain tissue.

Housing 512 is positioned at tissue 501 such that a surface 513 of housing 512 contacts surface 503 of tissue 501. Light emission area 112, first reception area 114, and second reception area 115 are provided at surface 513. In the illustrated example, light source 113, first photodetector 116, and second photodetector 117 are also provided at surface 513. For instance, light emission and reception areas 112, 114, 115 may be constituted by a respective active area of light source 113 and photodetectors 116, 117. Other components of hearing device 101 may be accommodated in an inner volume 515 enclosed by housing 512. Light source 113 can thus be configured to provide light emitted from light emission area 112 at housing 515 which is illuminating an illumination volume 514 extending into tissue 501. In the schematic illustration, illumination volume 514 is indicated as a volume of a light cone of the light emitted at light emission area 112. Illumination volume 514 may be defined more generally as a volume through which light emitted from light emission area 112 propagates. In the schematic illustration in FIG. 8A, illumination volume 514 may be regarded as a volume that would be illuminated by the emitted light when disregarding an interaction of the emitted light with tissue 501, for example corresponding to a situation in which housing 512 would be removed from tissue 501, and/or before the emitted light would interact with tissue 501, for example scattered and/or absorbed by tissue 501. When housing 512 is positioned at tissue 501, illumination volume 514 may be altered corresponding to an interaction of the emitted light with the tissue.

A first acceptance volume 516 from which light can arrive in order to be detectable by first photodetector 116, and a second acceptance volume 517 from which light can arrive in order to be detectable by second photodetector 117 may be defined correspondingly as a volume through which light received at reception areas 114, 115 propagates before detection by photodetectors 116, 117. Acceptance volumes 516, 517 are also schematically illustrated in FIG. 8A as a respective light cone detectable be photodetectors 116, 117. In the schematic illustration, acceptance volumes 516, 517 may be regarded as a volume from which light detectable by photodetector 116, 117 may arrive at reception areas 114, 115 by disregarding an interaction of the light with tissue 501, for example corresponding to a situation in which housing 512 would be removed from tissue 501, and/or after the detectable light has been scattered by tissue 501 toward reception areas 114, 115 in order to be detected by photodetector 116, 117. When housing 512 is positioned at tissue 501, acceptance volume 516, 517 may be altered corresponding to an interaction of the light detectable by photodetector 116, 117 with the tissue. First acceptance volume 516 includes first reception area 114 at housing 512 having first distance d1 from light emission area 112, and second acceptance volume 517 includes second reception area 115 at housing 512 having second distance d2 from light emission area 112. For instance, first distance d1 may be defined as a distance between a center 522 of light emission area 112 and a center 524 of first reception area 114, and second distance d2 may be defined as a distance between the center 522 of light emission area 112 and a center 525 of second reception area 115. First acceptance volume 516 and second acceptance volume 517 extend into tissue 501 when housing 512 is worn at the ear.

The light emitted at light emission area 112 into tissue 501 within illumination volume 514 may then be scattered and/or absorbed by tissue 501. An amount of the scattering and/or absorption can depend on a wavelength of the emitted light and/or other properties of the emitted light such as a propagation direction and/or velocity of a respective photon of the light. In particular, an amount of the absorption can depend on the wavelength of the emitted light corresponding to a wavelength at which the light can be absorbed by an analyte contained in the tissue. The amount of the absorption also depends on a concentration of the analyte in the tissue. Determining an amount of absorption of the emitted light in the tissue at a specific wavelength can thus allow to draw conclusions about the concentration of the respective analyte in the tissue.

Furthermore, the amount of the absorption by an analyte and scattering inside the tissue can increase with an increasing distance of the light propagating in tissue 501, since the longer the light travels inside tissue 501 the larger the probability of encountering an absorbing analyte or being scattered in the tissue. Detecting the light received at different distances d1, d2 can indicate an amount of attenuation of the light depending on the distance, which may be caused by the absorption and/or scattering. This can allow to draw conclusions about the concentration of the respective analyte in the tissue by taking into account the difference between distances d1, d2. In some instances, distances d1, d2 may be selected to be close enough such that a difference in attenuation determined at the different distances d1, d2 may by mainly attributed to the scattering inside the tissue. An amount of the emitted light that has been absorbed by the analyte in the light detected at the different distances d1, d2 may then be substantially equal.

In order to be received at different distances d1, d2, an unabsorbed part of the emitted light can be scattered by tissue 501 into first acceptance volume 516 to be received at first reception area 114 and detected by first photodetector 116, and another unabsorbed part of the emitted light can be scattered by tissue 501 into second acceptance volume 517 to be received at second reception area 115 and detected by second photodetector 117. An exemplary spatial distribution of possible and/or most probable pathways 528 of light emitted at a specific point at light emission area 112 arriving at a specific point at first reception area 114 or at a specific point at second reception area 115 by means of scattering processes inside tissue 501 is schematically indicated as a shaded area. As illustrated, spatial light path distribution 528 can reach into outer tissue layer 504 and inner tissue layer 506.

In the illustrated example, first and second reception areas 114, 115 are spaced apart from light emission area 112 at distances d1, d2 extending at least partially in a rectilinear direction. More generally, a direction of extension of distances d1, d2 may include, as indicated, a rectilinear directional component, and may, in some instances, further include a curvilinear directional component and/or a circumferential directional component. For instance, the spacing between light emission and reception areas 112, 114, 115 may be provided along surface 304, 305 of housing 311, 321, 331, 341, 351, 361 configured to be worn behind the ear, or at least partially in the direction of central axis 405 along surface 404 of housing 411, 421, 431, 441, 451, 461 configured to be at least partially inserted into the ear canal.

Figure 8B:
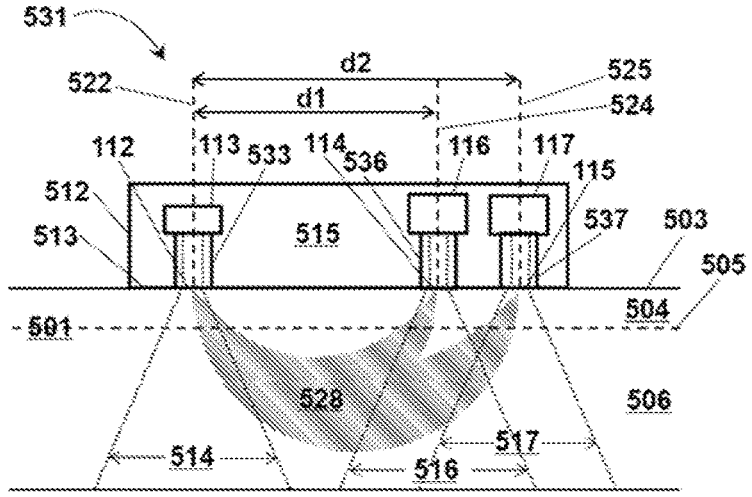

FIG. 8B illustrates another measurement arrangement 531 in which housing 512 of hearing device 101 is worn at the ear. Light source 113 and photodetectors 116, 117 are accommodated in inner space 515 enclosed by housing 512. A first light guide 533 is arranged between light source 113 and light emission area 112. Light provided by light source 113 can thus be conducted to light emission area 112 by first light guide 533. A second light guide 536 is arranged between first reception area 114 and first photodetector 116, and a third light guide 537 is arranged between second reception area 115 and second photodetector 117. Light received at first and second reception area 114, 115 can thus be conducted to first and second photodetector 116, 117 by second and third light guide 536, 537. Light guides 533, 536, 537 are configured to transmit light at at least one wavelength or a wavelength range of the light provided by light source 113 and detectable by photodetectors 116, 117. The wavelength range may comprise at least two wavelengths, or at least three wavelengths, of light absorbable by different analytes in the tissue. For instance, light guides 533, 536, 537 may be formed of a transparent or translucent material. Light guides 533, 536, 537 may also be provided as light conducting fibers.

In some instances, a transparent cover glass with a rather high light transmission coefficient may be integrated at light emission and detection areas 112, 114, 115 at the end of a respective light guide 533, 536, 537, in particular at the end of light conducting fibers implemented in light guide 533, 536, 537. This can protect the sensor unit from moisture and/or maximize the light transmission into and from the tissue. The cover glass may be selected to act as an index matching object to improve the optical interface, which can reduce a measurement error, increase the detection efficiency and enhance the net attribute signal. In order to minimize the transmission loss due to reflection from the glass surfaces, the cover glass may be chosen as thin as possible.

In some instances, light guides 533, 536, 537 may be omitted. Light emission and reception areas 112, 114, 115 may then each be provided as a transparent or translucent window, in particular an aperture, in housing 512 leading to surface 513. Light source 113 and photodetectors 116, 117 may be arranged close to the respective window or spaced apart from the window.

Figure 8C:
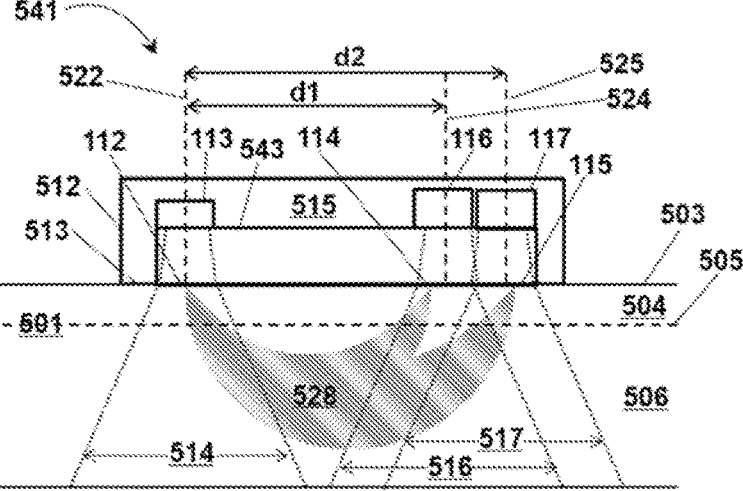

FIG. 8C illustrates another measurement arrangement 541 in which housing 512 of hearing device 101 is worn at the ear. A single light guide 543 is arranged between light emission and reception areas 112, 114, 115 and light source 113 and photodetectors 116, 117. Light guide 543 is configured to preserve a propagation direction of the incoming light when the light propagates through light guide 543, at least to a certain extent, such that light received at reception areas 114, 115 and detected by photodetectors 116, 117 is representative of different spatial locations at different distances d1, d2. For instance, light guide 543 may be implemented as sealing member 175 illustrated in FIGS. 4B, 4C, which may be formed of a transparent or translucent material. Light source 113 and photodetectors 116, 117 may then be provided at a side of sealing member 175 opposing light emission and reception areas 112, 114, 115 at sealing member 175, for instance at surface 174 of body portion 173 or accommodated inside body portion 173 of the hearing device. In some instances, as illustrated, first reception areas 114 and second reception area 115 may partially overlap such that light received at both reception areas may be partially detectable by both photodetectors 116, 117. First and second reception areas 114, 115, however, do not fully overlap such that photodetectors 116, 117 can receive a different signal representing different spatial locations at different distances d1, d2. In some examples, center 524 of first reception area 114 is separate from second reception area 115, and center 525 of second reception area 115 is separate from first reception area 114.

In some instances, a light barrier may be provided in light guide 543 between light emission area 112 and reception areas 114, 115. In this way, a cross talk between the light emitted by light source 113 and detected by photodetectors 116, 117 without passing through tissue 501, in particular without passing through deeper layers of tissue 501, can be minimized.

Figure 8D:
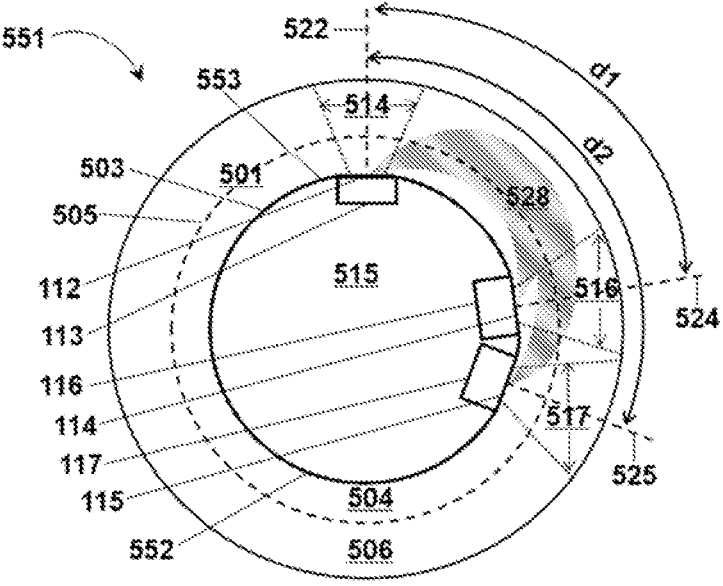

FIG. 8D illustrates a measurement arrangement 551 in which a housing 552 of hearing device 101 is at least partially inserted inside an ear canal of the ear such that housing 552 is positioned at tissue 501 inside the ear canal. Housing 552 comprises a curved surface 553 at least partially contacting a wall of the ear canal. First and second reception areas 114, 115 are spaced apart from light emission area 112 at distances d1, d2 extending at least partially in a curvilinear direction along a circumference of curved surface 553. In the schematic illustration, distances d1, d2 along curved surface 553 are not reproduced true to scale. More generally, a direction of extension of distances d1, d2 may include, as indicated, a curvilinear directional component, and may, in some instances, further include a rectilinear directional component, as indicated in FIG. 8A. For instance, the spacing between light emission and reception areas 112, 114, 115 may be provided at least partially in the direction of circumference 406 along surface 404 of housing 411, 421, 431, 441, 451, 461 configured to be at least partially inserted into the ear canal. Distances d1, d2 may also extend at least partially in a curvilinear direction along a curvature of surface 304, 305 of housing 311, 321, 331, 341, 351, 361 configured to be worn behind the ear.

Figure 8E:
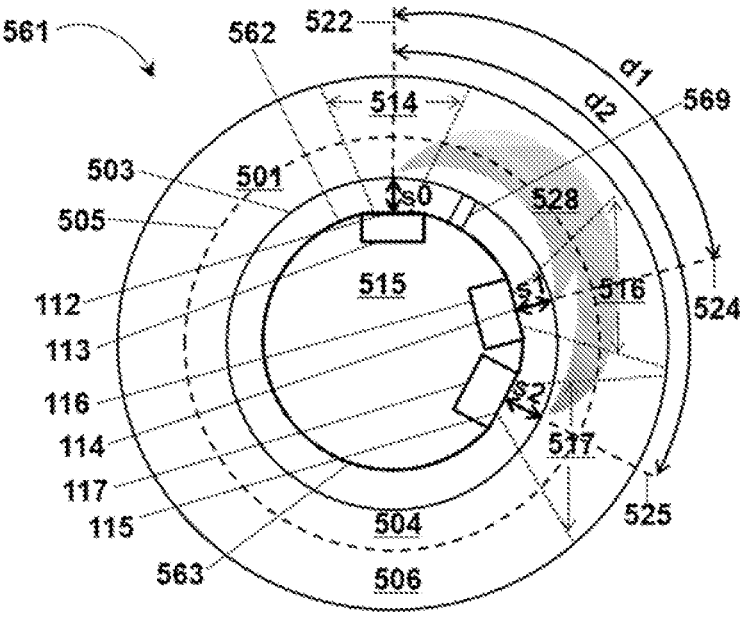

FIG. 8E illustrates a measurement arrangement 561 in which another housing 562 of hearing device 101 is at least partially inserted inside the ear canal. Housing 552 comprises a curved surface 563 spaced from the ear canal wall. Light emission and reception areas 112, 114, 115 are spaced from surface 503 of tissue 501 by a respective distance s0, s1, s2. Light emitted at light emission area 112 thus propagates through an empty space along distance s0 before entering tissue 501. Light scattered by tissue 501 toward reception areas 114, 115 propagates through an empty space along distances s1, s2 before being received at reception areas 114, 115. For instance, light emission and reception areas 112, 114, 115 may be provided at body portion 174 of housing 171 illustrated in FIG. 4B at distances s0, s1, s2 from tissue 501. In some instances, distances s0, s1, s2 are selected to be substantially equal. In some instances, as illustrated, a light barrier 569 extending through the spacing between surface 563 of housing 552 and surface 503 of tissue 501 may be provided between light emission area 112 and reception areas 114, 115. Thus, a cross talk between the light emitted by light source 113 and detected by photodetectors 116, 117 without passing through tissue 501 can be minimized.

Figure 8F:
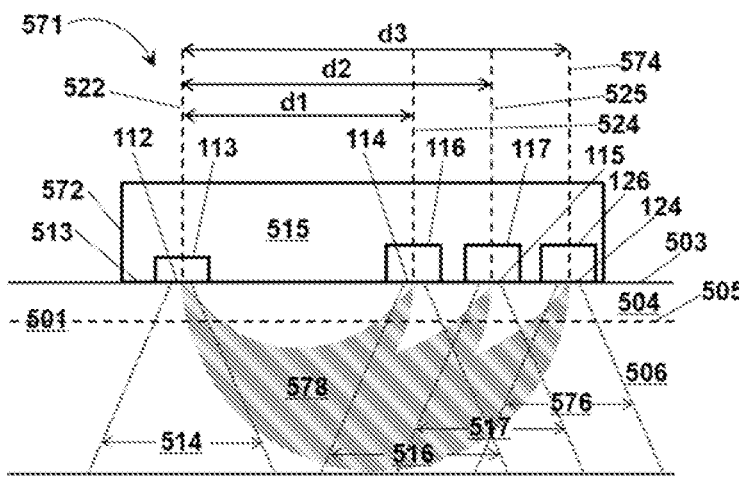

FIG. 8F illustrates a measurement arrangement 571 in which a housing 572 of hearing device 101 is worn at an ear such that housing 512 is positioned at tissue 501. Third reception area 124 is provided at surface 513 of housing 572 at distance d3 from light emission area 112 different from distances d1, d2. In the illustrated example, third photodetector 126 is also provided at surface 513. In other examples, third photodetector 126 can be accommodated in inner space 515 of housing 572, corresponding to the arrangement of first and second photodetectors 116, 117 in measurement arrangement 531, 541. Sensor unit 125, as illustrated in FIG. 2B, may be implemented correspondingly. A third acceptance volume 576 from which light can arrive in order to be detectable by third photodetector 126 thus comprises third reception area 124 at surface 513. Third acceptance volume 576 extends into tissue 501 such that a part of the light emitted at light emission area 112 scattered by tissue 501 into third acceptance volume 576 is contributing to the light detectable by third photodetector 126.

An exemplary spatial distribution of possible and/or most probable pathways 578 of light emitted at a specific point at light emission area 112 arriving at a specific point at first reception area 114 or at a specific point at second reception area 115 or at a specific point at third reception area 124 is schematically indicated as a shaded area. As illustrated by spatial light path distribution 578 as compared to spatial light path distribution 528 illustrated in FIGS. 8A-E, providing third reception area 124 at third distance d3 in addition to first and second reception areas 114, 115 at distances d1, d2 can not only allow to enhance information about a spatial dependency of the light interacting with the tissue, but also to collect additional information about deeper located portions and/or layers of tissue 501.

In the illustrated example, distances d1, d2, d3 of reception areas 114, 115, 124 from light emission area 112 at distances d1, d2 extend at least partially in a rectilinear direction, corresponding to measurement arrangement 521, 531, 541 illustrated in FIGS. 8A-C. For instance, the spacing between light emission and reception areas 112, 114, 115, 124 may be provided along surface 304, 305 of housing 311, 321, 331, 341, 351, 361 configured to be worn behind the ear, or at least partially in the direction of central axis 405 along surface 404 of housing 411, 421, 431, 441, 451, 461 configured to be at least partially inserted into the ear canal. In other examples, distances d1, d2, d3 of reception areas 114, 115, 124 from light emission area 112 at distances d1, d2 extend at least partially in a curvilinear direction, corresponding to measurement arrangement 551, 561 illustrated in FIGS. 8D, 8E. For instance, the spacing between light emission and reception areas 112, 114, 115, 124 may be provided at least partially in the direction of circumference 406 along surface 404 of housing 411, 421, 431, 441, 451, 461 configured to be at least partially inserted into an ear canal, or along a curvature of surface 304, 305 of housing 311, 321, 331, 341, 351, 361 configured to be worn behind the ear.

Figure 8G:
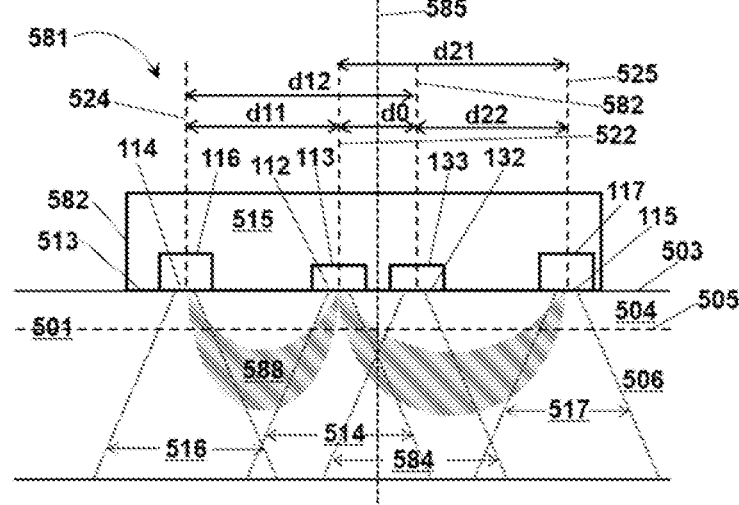

FIG. 8G illustrates a measurement arrangement 581 in which a housing 582 of hearing device 101 is worn at an ear positioned at tissue 501. Second light emission area 132 is provided at surface 513 of housing 582 at a distance d0 from first light emission area 112. For instance, distance d0 may be defined as a distance between center 522 of first light emission area 112 and a center 582 of second light emission area 132. Sensor unit 135, as illustrated in FIG. 2C, may be implemented correspondingly. In the illustrated example, second light source 133 is also provided at surface 513. In other examples, second light source 133 can be accommodated in inner space 515 of housing 582, corresponding to the arrangement of light source 113 in measurement arrangement 531, 541. First distance d12 of first reception area 114 from second light emission area 132 is equal to second distance d21 of second reception area 115 from first light emission area 112, and second distance d22 of second reception area 115 from second light emission area 132 is equal to first distance d11 of first reception area 114 from first light emission area 112. In this way, a symmetric arrangement of light emission and reception areas 112, 114, 115, 132 can be provided relative to a vertical axis 585 extending through a center of distance d0 between light emission areas 112, 132, and, correspondingly, through a center of a distance between reception areas 114, 115. A first illumination volume corresponds to illumination volume 514 through which light emitted from first light emission area 112 propagates, and a second illumination volume 584 corresponds to a volume through which light emitted from second light emission area 112 propagates.

FIG. 8G illustrates a measurement process at a first time, at which light is emitted from first light emission area 112. Light emission from second light emission area 132 can be impeded at the second time such that light is only emitted into tissue 501 from first light emission area 112. For instance, hearing device 101 may be configured to control second light source 133 to refrain from providing light at the first time. A corresponding exemplary spatial distribution of possible and/or most probable pathways 588 of light emitted at a specific point at first light emission area 112 at the first time arriving at a specific point at first reception area 114 or at a specific point at second reception area 115 is schematically indicated as a shaded area. At a second time different from the first time, light is emitted from second light emission area 112. Light emission from first light emission area 112 can be impeded at the second time such that light is only emitted into tissue 501 from second light emission area 112. For instance, hearing device 101 may be configured to control first light source 113 to refrain from providing the light at the second time. A corresponding spatial distribution of possible and/or most probable pathways of light emitted at a specific point at second light emission area 132 at the second time arriving at a specific point at first reception area 114 or at a specific point at second reception area 115 can look similar to spatial pathway distribution 588 mirrored at vertical axis 585, due to the symmetry of measurement arrangement 581.

Hearing device 101 may thus be configured to control light sources 113, 114 to switch between providing light only to first light emission area 112 at the first time, and providing light only to second light emission area 132 at the second time. In some instances, the controlling of light sources 113, 114 may be performed by processing unit 104 and/or processing unit 114. In this way, twofold measurement data can be obtained by the light detected by light detectors 116, 117 at the first time and at the second time. Due to the symmetry of measurement arrangement 581 with respect to vertical axis 585, the measurement data obtained at the two different times contains corresponding information about an impact of tissue 501 on the emitted light after propagating equal distances d11, d22, and after propagating equal distances d12, d21. Differences in the corresponding information obtained at the two different times may thus be attributed to unknown parameters which may be unrelated to the tissue properties but may also influence the measurement data. Those unknown parameters may include intrinsic characteristics of light sources 113, 133 and/or photodetectors 116, 117 and/or other unknown characteristics of the optical setup. An individual calibration of the sensor arrangement of light emission and reception areas 112, 114, 115, 132 in the measurement arrangement 581 with respect to those parameters prior to the measurement may thus not be required. Instead, the sensor arrangement may be implemented in a self-calibrating manner.

In the illustrated example, distances d11, d12, d21, d22 of reception areas 114, 115 from light emission areas 112, 132 extend at least partially in a rectilinear direction, corresponding to measurement arrangement 521, 531, 541 illustrated in FIGS. 8A-C. For instance, the spacing between light emission and reception areas 112, 114, 115, 132 may be provided along surface 304, 305 of housing 311, 321, 331, 341, 351, 361 configured to be worn behind the ear, or at least partially in the direction of central axis 405 along surface 404 of housing 411, 421, 431, 441, 451, 461 configured to be at least partially inserted into the ear canal. In other examples, distances d11, d12, d21, d22 of reception areas 114, 115 from light emission areas 112, 132 extend at least partially in a curvilinear direction, corresponding to measurement arrangement 551, 561 illustrated in FIGS. 8D, 8E. For instance, the spacing between light emission and reception areas 112, 114, 115, 132 may be provided at least partially in the direction of circumference 406 along surface 404 of housing 411, 421, 431, 441, 451, 461 configured to be at least partially inserted into an ear canal, or along a curvature of surface 304, 305 of housing 311, 321, 331, 341, 351, 361 configured to be worn behind the ear.

Figure 9:
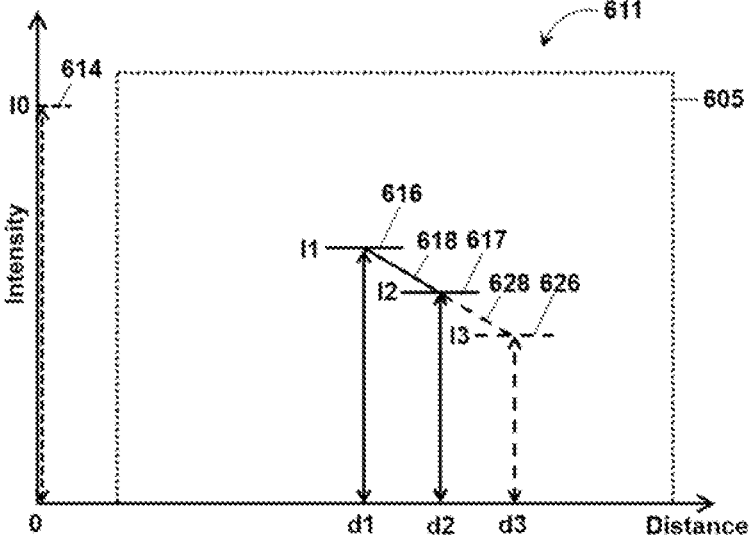
FIG. 9 schematically illustrates an exemplary graph of measurement data that may be obtained by any of the embodiments of a sensor unit illustrated in FIGS. 2A-C.

FIG. 9 schematically illustrates a graph 611 of measurement data 616, 617, 626 that may be obtained by means of sensor unit 105, 115, 125, 135, for instance when applied in measurement arrangement 521, 531, 541, 551, 561, 571, 581. Possible distances between light emission area 112, 132 and reception area 114, 115, 124 of sensor unit 105, 115, 125, 135 are horizontally indicated on an axis of abscissas. An intensity of light detectable by photodetectors 116, 117, 126 is vertically indicated on an axis of ordinates. Further indicated on the axis of abscissas is an actual value of distance d1 between light emission area 112 and first reception area 114, and an actual value of distance d2 between light emission area 112 and second reception area 115, as implemented in sensor unit 110, 125. An actual value of distances d11, d22 implemented in sensor unit 135 may correspond to the illustrated value of distance d1, and an actual value of distances d12, d21 implemented in sensor unit 135 may correspond to the illustrated value of distance d2. An actual value of distance d3 between light emission area 112 and third reception area 114, as implemented in sensor unit 125, is also indicated on the axis of abscissas. Accordingly, distances d1, d11, d22, d2, d12, d21, d3 can have a fixed value, as illustrated, which is predetermined according to their implementation in sensor unit 105, 115, 125, 135. In some instances, sensor data 141, 142, 143 provided by photodetectors 116, 117, 126 to processing unit 104, 114 may comprise information representative of the light intensity detected by photodetectors 116, 117, 126, and processing unit 104, 114 may be configured to associate the respective light intensity with distance d1, d11, d22, d2, d12, d21, d3 of reception area 114, 115, 124 at which the detected light has been received.

The measurement data comprises a first data value 616 including a first intensity I1 of light detected by first photodetector 116 associated with distance d1, and a second data value 617 including a second intensity I2 of light detected by second photodetector 117 associated with distance d2. When sensor unit 135 is employed, first data value 616 can comprise twofold information of first intensity I1 associated with distance d11 and second intensity I2 associated with distance d22, which may be determined at two different times, and second data value 617 can comprise twofold information of first intensity I1 associated with distance d12 and second intensity I2 associated with distance d21, which may also be determined at the two different times. The measurement data may comprise a third data value 626 including a third intensity I3 of light detected by third photodetector 126 associated with distance d3, for instance when sensor unit 125 is employed, or when a combination of sensor units 125, 135 is employed, which may include two light emission areas 112, 132 and three reception areas 114, 115, 124.

An intensity I0 of the light emitted at light emission area 112, 132 is indicated by a data point 614, which may serve as a reference with respect to measurement data 616, 617, 627 associated with a distance value of zero. Determining a value of intensity I0, however, may not be required to determine a property of the tissue based on measurement data 616, 617, 626, as further detailed below. A distance region 605 in which measurement data 616, 617 may be impacted by an interaction with a deeper region of the tissue at the ear, and not only be reflected from a surface region of the tissue, is schematically indicated as a dotted box. At rather short distances between light emission and detection areas 112, 114, 115, 132, measurement data 616, 617 may not include useful information about an interaction of the emitted light with the deeper layers inside the tissue, but may mostly represent light reflected at superficial layers of the skin tissue.

A gradient 618 between intensities I1, I2 may be determined by taking into account the difference between distances d1, d2, which may be determined as a value of (d2−d1), or (d1−d2). When sensor unit 125 is employed, a gradient 628 between intensities I2, I3 may also be determined by taking into account the difference between distances d2, d3, which may be determined as a value of (d3−d2), or (d2−d3).

To illustrate, a reflectance R may be generally defined for an intensity I of the detected light as $$R = \frac{I}{I0}$$

such that a first reflectance R1 for the detected light received at first distance d1 may be determined as (R1=I1/I0), and a second reflectance R2 for the detected light received at second distance d2 may be determined as (R2=I2/I0). When sensor unit 125 is employed, a third reflectance R3 for the detected light received at third distance d3 may be determined as (R3=I3/I0). An attenuation A of the detected light received at the different distances may be generally defined depending on the reflectance R as $$A = -\log(R)$$

such that a first attenuation A1 for the detected light received at first distance d1 may be determined as A1=−log(R1), and a second attenuation A2 for the detected light received at second distance d2 may be determined as A2=−log(R2). When sensor unit 125 is employed, a third attenuation A3 for the detected light received at third distance d3 may be determined as A3=−log(R3). Thus determined values A1, A2, A3 of the attenuation A may be plotted in graph 611 in the place of the respective intensities I1, I2, I3. Gradient 618 of the attenuation A may then be determined based on attenuation values A1 and A2 by taking into account the difference between distances d1, d2 as $$\frac{\partial A}{\partial d} = \frac{A2 - A1}{d2 - d1}.$$

In some instances, gradient 618 of the attenuation A may also be expressed depending on intensities I1, I2 as $$\frac{\partial A}{\partial d} = \frac{\log\left(\frac{I1}{I2}\right)}{d2 - d1}$$

independently of intensity I0 of the emitted light. When sensor unit 125 is employed, gradient 628 of the attenuation A may be determined correspondingly based on attenuation values A2 and A3 by taking into account the difference between distances d2, d3. Generally, reflectance R, attenuation A, and gradients 618, 628 also depend on a wavelength λ of the detected light, in particular due to an absorption of the light by analytes contained in the tissue at a specific value of the wavelength λ.

The difference of distances d1, d2 and/or the difference of distances d2, d3 can also be representative for a difference of a mean pathlength of the emitted light inside the tissue and/or a difference of a mean time of the emitted light remaining inside the tissue before the light is received at the respective distance d1, d2, d3 and detected by the respective photodetector 116, 117, 126. Generally, due to multiple scattering, the physical pathlength traveled by the light through the tissue can be considerably larger than distances d1, d2, d3 between light emission and detection areas 112, 114, 115, 132, but can be assumed to be directly proportional to the respective distance d1, d2, d3. In some instances, the difference between distances d1, d2, d3 may be selected to be small enough to account for similar properties of the tissue. In some instances, the difference between distances d1, d2, d3 may be selected to be small enough such that an absorption of the light by the analyte is substantially equal prior to the detection of the light at the distances d1, d2, d3. Differences in the light attenuation of the light detected at the different distances d1, d2, d3 may then be mainly attributed to in increased amount of scattering occurring inside the tissue when the light is travelling a longer distance.

In some instances, in particular when sensor units 115, 125 illustrated in FIGS. 2A, 2B are employed, a distance between reception areas 114, 115, 124 may also be selected to be rather small in order to reduce disturbing effects such as topical interferents on the surface of the tissue and/or anatomical differences within the optical path inside the tissue and/or a cross talk between light emission area 112 and reception areas 114, 115, 124 without the light entering and propagating through the tissue. In some other instances, in particular when sensor unit 135 illustrated in FIG. 2C is employed, reception areas 114, 115, 124 may be spaced apart at a larger distance, wherein the twofold detection of the light at the different times may be exploited to cancel at least some of those unknown influences in a self-calibrating manner.

The larger the difference of the mean pathlength and/or the mean time in which the emitted light remains inside the tissue, the higher the probability that the emitted light is absorbed by an analyte contained in the tissue at a specific wavelength λ absorbable by the analyte. Gradient 618, 628 can thus be indicative of a concentration C of the analyte contained in the tissue. For instance, a concentration C(water) of water contained inside the tissue may be determined based on gradient 618, 628 for the light detected at a wavelength λ of 970 nm and/or 1400 nm and/or 1450 nm and/or 1500 nm, or at a wavelength deviating from the respective value of λ by at most 20 nm. A concentration C(Hb) of haemoglobin contained inside the tissue may be determined based on gradient 618, 628 for the light detected at a wavelength λ of about 810 nm and/or 660 nm and/or 880 nm and/or 940 nm, or at a wavelength deviating from the respective value of λ by at most 10 nm. A concentration C(lipid) of a lipid contained inside the tissue may be determined based on gradient 618, 628 for the light detected at a wavelength λ of about 1200 nm, or at a wavelength deviating from this value of λ by at most 20 nm. A concentration C(glucose) of glucose contained inside the tissue may be determined based on gradient 618, 628 for the light detected at a wavelength λ of about 1650 nm, or at a wavelength deviating from this value of λ by at most 50 nm.

In some implementations, an absolute value of the concentration C can be quantitatively estimated from gradient 618, 628, which may be derived based on a physical model considering various interactions of the light with the tissue, in particular light absorption and emission and scattering processes, when the light is propagating inside the tissue. The physical model may be based on a radiative transfer equation, which may be approximated by a diffusion equation, as described, for instance, in the textbook "Biomedical Optics: Principles and Imaging" by Lihong V. Wang and Hsin-i Wu, first published by John Wiley & Sons on 15 Jul. 2009, ISBN: 978041743040, DOI: 10.1002/9780470177013. In particular, the concentration C may be derived from an analytical approximation of a solution of the equation, or a numerical method of solving the equation such as, for instance, a Monte Carlo algorithm simulating the light interaction inside the tissue. In some implementations, a relative value of the concentration C can be qualitatively estimated from gradient 618, 628 in order to determine a property of the tissue based on the relative value.

In some implementations, light source 113, 133 is configured to provide light at different wavelengths each absorbable by a different analyte contained in the tissue. Photodetectors 116, 117, 126 may then be configured to detect the light separately at the different wavelengths. In this way, a concentration of a plurality of analytes contained in the tissue may be determined. In some instances, light source 113 is configured to provide the light at at least one wavelength λ absorbable by water, and at at least one other wavelength λ absorbable by an analyte different from water, in particular haemoglobin and/or a lipid and/or glucose. Thus, the concentration C(water) of water as a first analyte can be related to the concentration C(secondary) of the different analyte as a second analyte. This may be exploited to determine a hydration index HI indicative of a hydration level of the user wearing the hearing device. The hydration index HI may be defined as a concentration C(water) of water contained in the tissue relative to a concentration C(secondary) of at least one analyte different from water contained in the tissue. In some instances, the hydration index HI may be determined as $$ HI = \frac{C(\text{water})}{C(\text{water}) - C(\text{secondary})}, $$

wherein C(secondary) may correspond to the concentration C(Hb) of haemoglobin, or the concentration C(lipid) of a lipid, or the concentration C(glucose) of glucose. In some instances, concentrations C(secondary) of multiple analytes different from water can be determined, which may be employed to determine the hydration index HI at a higher certainty.

In some exemplary configurations, light source 113 may be provided to provide the light with emission peaks at wavelengths of 940 nm, 970 nm, and 1000 nm, or at a wavelength deviating from the respective value of λ by at most 20 nm. When sensor unit 135 illustrated in FIG. 2C is employed, second light source 133 may be configured to provide the light correspondingly. In this way, light source 113, 133 can provide the light at wavelengths resolving a wavelength range of a strong absorption peak of water centered at 970 nm. In some other exemplary configurations, light source 113 may be provided to provide the light with emission peaks at wavelengths of 1300 nm, 1450 nm, and 1550 nm, or at a wavelength deviating from the respective value of λ by at most 20 nm. When sensor unit 135 illustrated in FIG. 2C is employed, second light source 133 may be configured to provide the light correspondingly. In this way, light source 113, 133 can provide the light at wavelengths resolving a wavelength range of a strong absorption peak of water centered at 1450 nm. The light intensity detected at the different wavelengths around the absorption peak at 970 nm and/or at 1450 nm may then be integrated over the wavelength in order to determine an area of the detected spectrum around the absorption peak. The concentration C(water) may thus be determined at high accuracy.

For instance, photodetectors 116, 117 may then be implemented with an active area comprising InGaAs. In some exemplary configurations, first distance d1, d11 of first photodetector to light source 113 may have a value of 6 mm, and second distance d2, d21 of second photodetector to light source 113 may have a value of 8 mm.

In some other exemplary configurations, light source 113 may be configured to provide the light with emission peaks at at least one wavelength absorbable by haemoglobin, and at at least one wavelength absorbable by water. For instance, the wavelength absorbable by haemoglobin may include a wavelength absorbable by both deoxyhaemoglobin and oxyhaemoglobin, such as a wavelength of 810 nm, or a wavelength deviating from this value by at most 10 nm, in order to determine C(Hb). For instance, the wavelengths absorbable by haemoglobin may include a wavelength absorbable by oxyhaemoglobin, such as a wavelength of 880 nm or 940 nm, or a wavelength deviating from this value by at most 10 nm, to determine a concentration of oxyhaemoglobin, and a wavelength absorbable by deoxyhaemoglobin, such as a wavelength of 660 nm, or a wavelength deviating from this value by at most 10 nm, to determine a concentration of deoxyhaemoglobin. C(Hb) may then be derived as the sum of the concentrations of oxyhaemoglobin and deoxyhaemoglobin. In addition to the determining of C(Hb), other blood properties such as at least one of a heart rate, a blood oxygen saturation level, and a blood pressure may be determined based on the detected wavelength absorbable by haemoglobin. Based on C(Hb) and C(water), the hydration index HI may be determined as described above.

In some other exemplary configurations, light source 113 may be configured to provide the light with emission peaks at at least one wavelength absorbable by lipid and/or at least one wavelength absorbable by glucose, and at at least one wavelength absorbable by water. After determining C(lipid) and C(water) and/or C(glucose) and C(water), the hydration index HI may be determined as described above. Other blood properties, such as a blood sugar level, may also be determined based on the detected wavelength absorbable by glucose. When sensor unit 135 illustrated in FIG. 2C is employed, second light source 133 may be configured to provide the light correspondingly. Light source 113, 133 can also be configured to provide the light at wavelengths absorbable by lipid and water to resolve an interaction between protein, lipid, and water. Such an interaction can lead to a disruption of the hydrogen bonding network in the tissue and therefore leads to corresponding changes of tissue properties such as a scattering coefficient, refractive index, etc., which consequently also affects the hydration index HI.

FIG. 10A illustrates a block flow diagram for an exemplary method of operating hearing device 101 and/or hearing system 100 to determine a property of a tissue at the ear at which a housing of hearing device 101 is worn. The method may be executed by processing unit 104 included in hearing device 101 and/or processing unit 114 included in communication device 111, in particular by executing the data processing algorithm illustrated in FIG. 3. At 711, light source 113 is controlled to provide light emitted at light emission area 112 to illuminate illumination volume 114 extending into tissue at the ear when the housing is worn at the ear. At 714, first photodetector 116 is controlled to detect a first light intensity of light received at first reception area 114 at first distance d1, d11 from light emission area 112 and to provide sensor data 141 indicative of the first light intensity. Concurrently, at 715, second photodetector 117 is controlled to detect a second light intensity of light received at second reception area 115 at second distance d2, d21 from light emission area 112 and to provide sensor data 142 indicative of the second light intensity. At 717, the first light intensity and the second light intensity are evaluated by taking into account the difference between first distance d1, d11 and second distance d2, d21. The detected first and second light intensity may thus be related to the difference between first distance d1, d11 and second distance d2, d21. Operation 717 may be performed by sensor data evaluation module 145. At 719, at least one property of the tissue at the ear is determined. Operation 719 may be performed by tissue property determination module 146.

Various configurations of light source 113 and photodetectors 116, 117 are conceivable. In some instances, light source 113 can be configured to emit light only at the first wavelength and only at the second wavelength, or only in a small wavelength range around the first wavelength and a small wavelength range around the second wavelength. For example, light source 113 may comprise two light source elements each providing the light at one of the two distinct wavelengths. In particular, light source 113 may be provided as an array of two LEDs emitting the light at the different wavelengths. Photodetectors 116, 117 can then detect light at least at the first wavelength and at the second wavelength, or at least in a small wavelength range around the first wavelength and a small wavelength range around the second wavelength. Photodetectors 116, 117 may also be configured to detect the light in a broader wavelength range, in particular a continuous wavelength range, spanning between the first and second wavelength. In some instances, when light source 113 comprises two light source elements, the light source elements can be spaced apart, wherein the distances d1, d2 of a light emission area of the light source element emitting at the first wavelength, and the distances d1, d2 of a light emission area of the light source element emitting at the second wavelength are taken into account separately when deriving the property of the tissue.

In some instances, light source 113 can be configured to emit light over a continuous wavelength range encompassing the first wavelength and the second wavelength. For example, light source 113 may be a single broadband light source. Photodetectors 116, 117 can then be configured to detect light only at the first wavelength and at the second wavelength, or only in a small wavelength range around the first wavelength and a small wavelength range around the second wavelength. For example, photodetectors 116, 117 may each comprise two photodetector elements each detecting the light at one of the two distinct wavelengths. In particular, photodetectors 116, 117 may be provided as an array of two photodetectors each detecting the light at one of the different wavelengths. In some instances, when each photodetector 116, 117 comprises two photodetector elements, the photodetector elements can be spaced apart, wherein the distances d1, d2 of the reception areas of the photodetector elements emitting at the first wavelength, and the distances d1, d2 of the reception areas of the photodetector elements emitting at the second wavelength are taken into account separately when deriving the property of the tissue. Photodetectors 116, 117 may also be configured to detect the light in a broader wavelength range, in particular a continuous wavelength range, spanning between the first and second wavelength. A filter may then be applied at light source 113 and/or at photodetectors 116, 117 which only allows passage of light at the first wavelength and only at the second wavelength, or only in a small wavelength range around the first wavelength and a small wavelength range around the second wavelength.

FIG. 10B illustrates a block flow diagram for an exemplary method of evaluating the first light intensity and the second light intensity in operation 717 of the method illustrated in FIG. 10A. At 727, a gradient is determined by relating a quantity derived from the first light intensity and the second light intensity to the difference between first distance d1, d11 and second distance d2, d21. The quantity may be derived from the first light intensity and the second light intensity in a preceding step 726. The quantity may comprise a difference of an attenuation A of the emitted light when received at the first reception area, as represented by the light detected by first photodetector 116, and the second reception area, as represented by the light detected by second photodetector 117. The quantity may also comprise a difference of a reflectance R of the light received at the first reception area and the second reception area. The quantity may also comprise a difference between the first intensity and the second intensity.

FIG. 10C illustrates a block flow diagram for another exemplary method of operating hearing device 101 and/or hearing system 100 to determine a property of a tissue at the ear. At 731, light source 113 is controlled to provide the light emitted at light emission area 112 at a first wavelength and at a second wavelength separate from one another. Each wavelength may be selected to be absorbable by an analyte contained in the tissue, in particular by different analytes. Operations 714, 715, 716 of the method illustrated in FIG. 10A are performed for the light emitted at the first wavelength. Corresponding operations 734, 735, 736 are also performed for the light emitted at the second wavelength including, at 734, 735, controlling first and second photodetector 116, 117 to detect the first and second light intensity at the second wavelength and to provide sensor data 141, 142 indicative of the detected light intensities, and, at 737, evaluating the first and second light intensity detected at the second wavelength by taking into account the difference between first distance d1, d11 and second distance d2, d21.

In some instances, light source 113 may be controlled at operation 731 to provide the light emitted at light emission area 112 at a third wavelength separate from the first and second wavelength, which may be selected to be absorbable by another analyte contained in the tissue or the same analyte which can absorb the first and/or second wavelength, wherein operations 714, 715, 716 are also correspondingly performed for the light emitted at the third wavelength. In particular, operations 726, 727 of the method illustrated in FIG. 10B may be performed for the light detected at each wavelength. Operation 719 of determining the at least one property of the tissue can then be performed based on the detected first and second light intensity related to the difference between first distance d1, d11 and second distance d2, d21 at each wavelength.

FIG. 10D illustrates a block flow diagram for an exemplary method of determining the at least one property of the tissue in operation 719. At 747, a concentration C of a first analyte contained in the tissue is determined based on the quantity derived from the first and second light intensity detected at the first wavelength related to the difference between distances d1, d11, d2, d21, as determined in operation 717. At 748, a concentration C of a second analyte contained in the tissue is determined based on the quantity derived from the first and second light intensity detected at the second wavelength related to the difference between distances d1, d11, d2, d21, as determined in operation 737. The first wavelength provided at operation 731 may be a wavelength absorbable by water. Thus, the concentration C(water) of water as the first analyte can be determined in operation 747. The second wavelength provided at operation 748 may be a wavelength absorbable by an analyte different from water. For instance, the second analyte may be a lipid or haemoglobin or glucose. Thus, the concentration C(secondary) of the second analyte can be determined in operation 748. At 749, a hydration index HI is determined based on the concentration C(water) of water, and the concentration C(secondary) of the second analyte.

FIG. 10E illustrates a block flow diagram for another exemplary method of determining the at least one property of the tissue in operation 719. At 757, a concentration C of an analyte contained in the tissue is determined based on the quantity derived from the first and second light intensity relative to the difference between distances d1, d11, d2, d21, as determined in operation 717 in the method illustrated in FIG. 10A, C or in operation 737 in the method illustrated in FIG. 10C. The light may be provided by light source 113 in operation 711, 731 at a wavelength absorbable by haemoglobin. Thus, the concentration C(haemoglobin) of haemoglobin can be determined in operation 757. The light may also be provided by light source 113 in operation 711, 731 at a wavelength absorbable by glucose. Thus, the concentration C(glucose) of glucose can be determined in operation 757. At 758, another property of blood flowing through the tissue is determined based on the first light intensity and/or second light intensity, as detected in any of operations 714, 715, 734, 735, and/or a quantity derived from the first and/or second light intensity. The blood property may comprise an oxygen saturation index (SpO2) and/or a blood pressure and/or a heart rate and/or a blood glucose level. In some instances, the hydration index HI is also determined. For instance, the method illustrated in FIG. 10E may be combined with the method illustrated in FIG. 10D by determining the concentration of the second analyte in operation 748 as the concentration C(haemoglobin) of haemoglobin performed in operation 757.

FIG. 10F illustrates a block flow diagram for another exemplary method of determining the at least one property of the tissue in operation 719. At 767, the property of the tissue is determined at a first time, and at 768, the property of the tissue is determined at a second time after the first time. Each time, the property may be determined based on the first light intensity and/or second light intensity, as detected in any of operations 714, 715, 734, 735, and/or a quantity derived from the first and/or second light intensity, at the respective time.

In some implementations, light source 113 is controlled in operation 711, 731 to provide the light at a constant intensity at each of the first and second time during a time interval in which the first light intensity is detected by the first photodetector and the second light intensity is detected by the second photodetector. In this way, a spatial resolution of the detected light received at distances d1, d11, d2, d21 may be obtained during each time by eliminating a temporal dependency of the emitted light intensity. This approach may be different from previously known time resolved PPG measurements in which a PPG waveform is obtained by controlling the light source to provide light with an intensity varying over time. For instance, light source 113 may be controlled in operation 711, 731 to provide the light at a constant intensity during a rather short signal pulse at each of the first and second time, wherein the light intensity may be varied between the different pulses.

At 769, a time dependent property of the tissue is determined based on the property determined at the first time at operation 767, and at the second time at operation 768, for instance by comparing the property obtained at the different times and/or deriving another quantity from the intensities detected at the different times. For example, a heart rate and/or blood pressure may be determined in operation 758 of the method illustrated in FIG. 10E corresponding to operation 769 of the method illustrated in FIG. 10F. At the same time, the concentration C of an analyte may be determined in operation 757 of the method illustrated in FIG. 10E and/or in operation 747 of the method illustrated in FIG. 10D based on the detected light received at different distances d1, d11, d2, d21 when the light has been emitted at a constant intensity during the first time and/or during the second time.

FIG. 10G illustrates a block flow diagram for another exemplary method of operating hearing device 101 and/or hearing system 100 to determine a property of a tissue at the ear. The method may be performed when employing sensor unit 125, as illustrated in FIG. 2B. At 776, third photodetector 126 is controlled to detect a third light intensity of light received at third reception area 124 at third distance d3 from light emission area 112 and to provide sensor data 143 indicative of the third light intensity. Operation 776 may be performed concurrently with operations 714, 715 of the method illustrated in FIG. 10A, C. Operation 776 may also be performed concurrently with operations 734, 735 of the method illustrated in FIG. 10C for the light detected at the second wavelength, wherein operation 731 may be employed in operation 711 to provide the light at the at least two different wavelengths. Operations 717, 719 may then be performed based on the detected light received at third distance d3, an addition to the detected light received at first distance d1, d11 and second distance d2, d21.

Figure 10H:
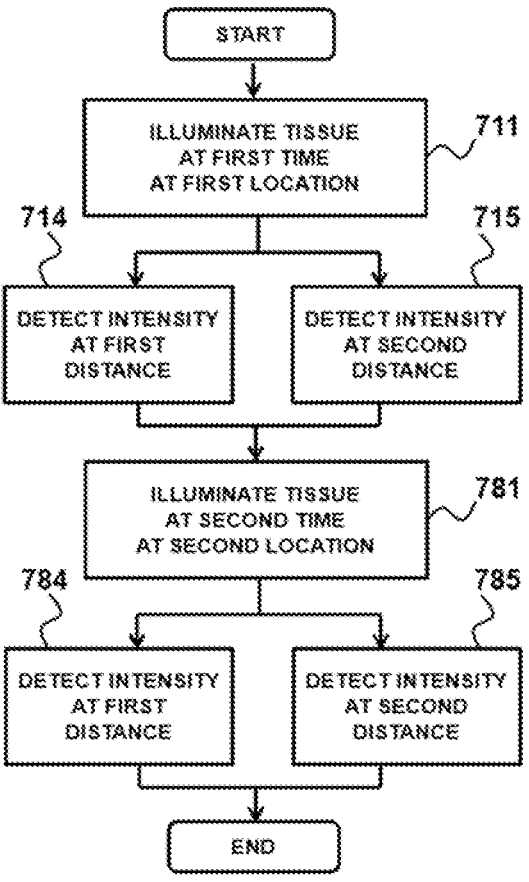

FIG. 10H illustrates a block flow diagram for another exemplary method of operating hearing device 101 and/or hearing system 100 to determine a property of a tissue at the ear. The method may be performed when employing sensor unit 135, as illustrated in FIG. 2C. During a first time, operations 711, 714, 715 are performed based on the light provided by first light source 113 emitted from first light emission area 112. During a second time after the first time, corresponding operations 781, 784, 785 are performed, wherein, at 781, in the place of first light source 113, second light source 133 is controlled to provide light emitted at second light emission area 132. At 784, first photodetector 116 is controlled to detect a first light intensity of light received at first reception area 114 at first distance d12 from light emission area 132 and to provide sensor data 141 indicative of the first light intensity detected at the second time. Concurrently, at 785, second photodetector 117 is controlled to detect a second light intensity of light received at second reception area 115 at second distance d12 from light emission area 112 and to provide sensor data 142 indicative of the second light intensity detected at the second time.

Subsequently, operation 717, 737 can be performed by employing the twofold information about the light intensities detected for equal distances d11, d22, and the twofold information about the light intensities detected for equal distances d12, d21, and relating a quantity derived from the light intensities to the difference between equal distances d11, d22 and equal distances d12, d21. Based on the quantity relative to the difference between the distances, a property of the tissue can be determined in operation 719, as described above. The method illustrated in FIG. 10H may thus be performed in the method illustrated in FIG. 10A by performing, after operations 711, 714, 715 have been performed at the first time, operations 781, 784, 785 at the second time. The method illustrated in FIG. 10H may also be performed in the method illustrated in FIG. 10C, wherein operation 781 may be performed by controlling second light source at the second time to provide the light at the at least two different wavelengths corresponding to the light provided by first light source 113 at the first time in operation 731, and by performing, after operations 714, 715 have been performed at the first time for the first wavelength, operations 781, 784, 785 at the second time for the first wavelength, and, after operations 734, 735 have been performed at the first time for the second wavelength, operations 781, 784, 785 at the second time for the second wavelength. The method illustrated in FIG. 10H may also be performed in the method illustrated in FIG. 10G by performing, after operations 711, 714, 715, 776 have been performed at the first time, operations 781, 784, 785 at the second time, wherein the light emitted in operation 781 at the second time may also be detected by third photodetector 126 at the second time, corresponding to operation 776.

While the principles of the disclosure have been described above in connection with specific devices, systems, and methods, it is to be clearly understood that this description is made only by way of example and not as limitation on the scope of the invention. The above described embodiments are intended to illustrate the principles of the invention, but not to limit the scope of the invention. Various other embodiments and modifications to those embodiments may be made by those skilled in the art without departing from the scope of the present invention that is solely defined by the claims. In the claims, the word "comprising" does not exclude other elements or steps, and the indefinite article "a" or "an" does not exclude a plurality. A single processing unit or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A hearing device comprising:
   a housing configured to be worn at an ear of a user;
   an output transducer configured to provide an audio signal to the user;
   a light source configured to provide light emitted from a light emission area at the housing, the light illuminating an illumination volume extending into tissue at the ear when the housing is worn at the ear;
   a first photodetector configured to detect a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area;
   a second photodetector configured to detect a second light intensity of light arriving from a second acceptance volume extending into tissue at the ear when the housing is worn at the ear such that a part of the emitted light scattered by the tissue into the second acceptance volume is contributing to the second light intensity, the second acceptance volume including a second reception area at the housing having a second distance from the light emission area different from the first distance; and
   a processing unit configured to determine a property of the tissue based on the first light intensity and the second light intensity by taking into account the difference between the first distance and the second distance.

2. The hearing device according to claim 1, wherein the processing unit is configured to determine, based on the first light intensity and the second light intensity, a difference in an attenuation of the light emitted from the light emission area between the first reception area and the second reception area.

3. The hearing device according to claim 1, further comprising:
   a third photodetector configured to detect a third light intensity of light arriving from a third acceptance volume extending into tissue at the ear when the housing is worn at the ear such that a part of the light scattered by the tissue into the third acceptance volume is contributing to the third light intensity, the third acceptance volume including a third reception area at the housing having a third distance from the light emission area different from the first distance and the second distance,
   wherein the processing unit is configured to determine the property of the tissue based on the third light intensity in addition to the first light intensity and the second light intensity.

4. The hearing device according to claim 1, wherein the light source is a first light source, the light emission area is a first light emission area, and the illumination volume is a first illumination volume, the hearing device further comprising:
   a second light source configured to provide light emitted from a second light emission area at the housing at a distance from the first light emission area, the light provided by the second light source illuminating a second illumination volume extending into tissue at the ear when the housing is worn at the ear such that a part of the light emitted from the second light emission area scattered by the tissue into the first acceptance volume is contributing to the first light intensity detected by the first photodetector, and a part of the light emitted from the second light emission area scattered by the tissue into the second acceptance volume is contributing to the second light intensity detected by the second photodetector, the first reception area having a distance from the second light emission area equal to the second distance, and the second reception area having a distance from the second light emission area equal to the first distance, wherein the first photodetector and the second photodetector are configured to detect the first light intensity and the second light intensity at a first time during which light is emitted from one of the first light emission area and the second light emission area, and at a second time different from the first time during which light is emitted from the other of the first light emission area and the second light emission area, and the processing unit is configured to determine the property of the tissue based on the first light intensity and the second light intensity detected at the first time and at the second time.

5. The hearing device according to claim 1, wherein the light source is configured to provide the light at a constant intensity during a time interval in which the first light intensity is detected by the first photodetector and the second light intensity is detected by the second photodetector.

6. The hearing device according to claim 1, wherein the processing unit is configured to determine a concentration of an analyte contained in the tissue.

7. The hearing device according to claim 1, wherein the light source is configured to emit light at a first wavelength and at a second wavelength different from the first wavelength.

8. The hearing device according to claim 7, wherein the processing unit is configured to determine, based on the first intensity and the second intensity detected at the first wavelength, a concentration of a first analyte contained in the tissue, and, based on the first intensity and the second intensity detected at the second wavelength, a concentration of a second analyte contained in the tissue.

9. The hearing device according to claim 8, wherein the processing unit is configured to determine, based on the concentration of the first analyte and the concentration of the second analyte, a hydration index of the tissue.

10. The hearing device according to claim 1, wherein the property is a first property, the processing unit configured to determine a second property of the tissue based on at least one of the first intensity or second intensity, wherein the second property comprises a property of blood flowing through the tissue.

11. The hearing device according to claim 1, wherein first distance and the second distance extend in different directions at the housing.

12. The hearing device according to claim 1, wherein the housing is configured to be worn behind the ear of the user.

13. The hearing device according to claim 12, wherein the light emission area, the first reception area, and the second reception area are provided at least one of at a portion of the housing oriented toward a head of the user when the housing is worn behind the ear or at a face of the housing at which the housing is supported on a top of the ear when the housing is worn behind the ear.

14. The hearing device according to claim 12, wherein at least one of the light emission area, the first reception area, or the second reception area is configured to be oriented toward the auricularis superior at the ear when the housing is worn behind the ear.

15. The hearing device according to claim 1, wherein the housing is configured to be at least partially inserted into an ear canal of the ear.

16. The hearing device according to claim 15, wherein at least one of the light emission area, the first reception area, or the second reception area is configured to be positioned at a bend of a wall of the ear canal when the housing is at least partially inserted into the ear canal.

17. The hearing device according to claim 1, wherein the first acceptance volume and the second acceptance volume are partially overlapping.

18. The hearing device according to claim 1, wherein:
the housing includes a first surface; and
the first photodetector and the second photodetector are each provided on the first surface of the housing.

19. A hearing system comprising:
a communication device; and
a hearing device communicatively coupled to the communication device, the hearing device including
  a housing configured to be worn at an ear of a user;
  an output transducer configured to provide an audio signal to the user;
  a light source configured to provide light emitted from a light emission area at the housing, the light illuminating an illumination volume extending into tissue at the ear when the housing is worn at the ear;
  a first photodetector configured to detect a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area;
  a second photodetector included in the hearing device, the second photodetector configured to detect a second light intensity of light arriving from a second acceptance volume extending into tissue at the ear when the housing is worn at the ear such that a part of the emitted light scattered by the tissue into the second acceptance volume is contributing to the second light intensity, the second acceptance volume including a second reception area at the housing having a second distance from the light emission area different from the first distance; and
  a processing unit included in the communications device, the processing unit configured to determine a property of the tissue based on the first light intensity and the second light intensity by taking into account the difference between the first distance and the second distance.

20. A method of determining a property of a tissue at an ear at which a housing of a hearing device is worn by a user, the method comprising:
  emitting light provided by a light source from a light emission area at the housing, the light illuminating an illumination volume extending into tissue at the ear when the housing is worn at the ear; and
  detecting, by a first photodetector, a first light intensity of light arriving from a first acceptance volume extending into tissue at the ear when the housing is worn at the ear such that a part of the emitted light scattered by the tissue into the first acceptance volume is contributing to the first light intensity, the first acceptance volume including a first reception area at the housing having a first distance from the light emission area;

detecting, by a second photodetector, a second light intensity of light arriving from a second acceptance volume extending into tissue at the ear when the housing is worn at the ear such that a part of the emitted light scattered by the tissue into the second acceptance volume is contributing to the second light intensity, the second acceptance volume including a second reception area at the housing having a second distance from the light emission area different from the first distance; and determining, based on the first light intensity and the second light intensity, the property of the tissue by taking into account the difference between the first distance and the second distance.

* * * * *